US007067322B2

(12) United States Patent
Corn et al.

(10) Patent No.: US 7,067,322 B2
(45) Date of Patent: *Jun. 27, 2006

(54) FUSION PROTEIN ARRAYS ON METAL SUBSTRATES FOR SURFACE PLASMON RESONANCE IMAGING

(75) Inventors: Robert M. Corn, Madison, WI (US); Emily A. Smith, Madison, WI (US); Bernard Weisblum, Madison, WI (US); Matthew G. Erickson, Madison, WI (US); Andrew T. Ulijasz, Madison, WI (US); Matthew J. Wanat, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 260 days.

This patent is subject to a terminal disclaimer.

(21) Appl. No.: 10/099,424

(22) Filed: Mar. 15, 2002

(65) Prior Publication Data

US 2003/0100127 A1 May 29, 2003

Related U.S. Application Data

(60) Provisional application No. 60/362,178, filed on Mar. 6, 2002, provisional application No. 60/304,246, filed on Jul. 10, 2001.

(51) Int. Cl.
*G01N 33/00* (2006.01)
*G01N 33/53* (2006.01)
*C07C 319/02* (2006.01)

(52) U.S. Cl. .................... 436/120; 436/119; 435/4; 435/7.1; 435/7.2; 435/DIG. 49; 568/18; 568/29

(58) Field of Classification Search .............. 435/3, 435/4, 6, 7.1, 7.2, 287.1, 287.2, 287.8, DIG. 49; 436/73, 86, 119, 120; 568/18, 29
See application file for complete search history.

(56) References Cited

U.S. PATENT DOCUMENTS 5,514,501 A * 5/1996 Tarlov ............................ 430/5
5,922,550 A * 7/1999 Everhart et al. ........... 435/7.21
6,127,129 A * 10/2000 Corn et al. ..................... 435/6

OTHER PUBLICATIONS

Willner et al., "Mediated Electron Transfer in Glutathione Reductace Organized in Self-Assembled Monolayered on AU Electrodes", 1992, JACS, 114, 10965-10966.*
Spinkle et al., "Molecular Recognition at Self-Assembled Monolayers; The Construction of Multicomponent Multilayers", 1993, Langmuir, 9, 1821-1825.*
Weetall, H. H., "Preparation of immobilized Proteins Covalently Coupled Through Silane Coupling Agents to Inorganic Supports", 1993, Applied Biochemistry and Biotechnology, 41, 157-188.*
Smith et al., "Formation, Spectroscopic Characterization, and Application of Sulfhydryl-Terminated Alkanethiol Monolayers for the Chemical Attachment of DNA onto Gold Surfaces", Apr. 17, 2001, 17(8):2502-2507.*
Julian et al., "A New Reagent Which May Be Used to Introduce Sulfhydryl Groups into Proteins, and Its Use in the Preparation of Conjugates for Immunoassay", 1983, Analytical Biochemistry, 132(1):68-73.*
Song et al., "Characterization of Cytochrome c/Alkanethiolate Structures Prepared by Self-Assembly on Gold", 1993, J. Phys. Chem., 97(24):6564-6572.*
Willner et al., "Mediated Electron Transfer in Glutathione Reductace Organized in Self-Assembled Monolayered on AU Electrodes", 1992, JACS, 114, 10965-10966.*
Amann et al. (1990) *J. Bacteriol.* 172:762-770.
Anderson et al. (2000) *Anal. Chem.* 72:3158-3164.
Arthur et al. (1992) *J. Bacteriol.* 174:2582-2591.
Barner et al. (1991) *Anal. Chem.* 63:55-60.
Brockman et al. (1999) *J. Am. Chem. Soc.* 121:8044-8051.
Brockman et al. (2000) *Ann. Rev. Phys. Chem.* 51:41:63.
Duffy et al. (1998) *Anal. Chem.* 70:4974-4984.
Effenhauser et al. (1997) *Anal. Chem.* 69:3451-3457.
Fodor (1997) *Science* 277:393-395.
Frey et al. (1995) *Anal. Chem.* 67:4452-4457.
Frutos et al. (1997) *Nucleic Acids Res.* 25:4748-4757.
Frutos et al. (1998) *J. Am. Chem. Soc.* 120:10277-10282.
Frutos et al. (1998) *Anal. Chem.* 70:449A-455A.
Frutos et al. (2000) *Langmuir* 16:2192-2197.
Gokce et al. (2000) *J. Mol. Biol.* 304:621-632.
Goss et al. (1991) *Anal. Chem.* 63:85-88.
Green et al. (1991) *Rev. Sci. Instrum.* 62:1426-1430.
Harboth et al. (2000) *J. Biol. Chem.* 275:31979-31985.
Herzog et al. (2000) *FEBS Lett.* 472:73-77.
Hickel et al. (1989) *Nature* 339:186.
Jo et al. (2000) *Microelectrochemical Systems* 9:76-81.
Jordan et al. (1997) *Anal. Chem.* 69:4939-4947.
Jordan & Corn (1997) *Anal. Chem.* 69(7):1449-1456.
Kohli et al. (1998) *J. Am. Chem. Soc.* 120:11962-11968.
Liedberg et al. (1983) *Sensors and Actuators* 4:299.
Lin et al. (2000) *Biochem.* 39:5104-5110.

(Continued)

*Primary Examiner*—Padmashri Ponnaluri
*Assistant Examiner*—My-Chau T. Tran
(74) *Attorney, Agent, or Firm*—Joseph T. Leone, Esq.; DeWitt Ross & Stevens S.C.

(57) ABSTRACT

Disclosed are methods for making surface plasmon resonance-capable arrays wherein molecules, such as proteins or nucleic acids, or cells, are adhered to a metal substrate. The metal substrates are modified by depositing an ω-modified alkanethiol monolayer to the substrate and then contacting the ω-modified monolayer with a heterobifunctional linking compound. Biomolecules or cells can then be attached to the heterobifunctional linking compound. Also disclosed are arrays wherein glutathione-containing molecules are immobilized on the substrate and GST-containing molecules are then specifically immobilized onto the substrate, taking advantage of the affinity between glutathione and GST.

13 Claims, 8 Drawing Sheets

OTHER PUBLICATIONS

Lockhart, et al. (1996) *Nature Biotechnology* 14:1675-1680.
Martzen et al. (1999) *Science* 286:1153-1155.
Nelson et al. (1999) *Anal. Chem.* 71:3928-3934.
Nelson et al. (2001) *Anal. Chem.* 73:1-7.
Partis et al. (1983) *J. Protein Chem.* 2:263-277.
Pease et al. (1994) *Proc. natl. Acd. Sci. USA* 91:5022-5026.
Quetglas et al. (2000) *PNAS* 97:9695-9700.
Rothenhausler & Knoll (1988) *Nature* 332:615-617.
Silin & Plant (1997) *Trends in Biotechnol.* 15.
Simons & Vander Jagt *Anal. Biochem* 82:334-341.
Strother et al. (2000a) *Nucleic Acids Research* 28:3535-3541.
Strother et al. (2000b) *J. Am. Chem. Soc.* 122:1205-1209.
Tarlov et al. (1993) *J. Am. Chem. Soc.* 115:5305-5306.
Thiel et al. (1997) *Anal. Chem.* 69:4948-4956.
Toribio et al. (1996) *J. Chrom. B* 684:77-97.
Thomas et al. (1995) *J. Am. Chem. Soc.* 117:3830-3834.
Winzeler et al. (1998) *Science* 281:1194-1197.
Youtani et al. (2000) *IUBMB Life* 49:27-31.

\* cited by examiner

500 μm

Surface Immobilized DNA:
- Sequence 1
- Sequence 2

SEQUENCE LISTING

<160> NUMBER OF SEQ ID NOS: 8

<210> SEQ ID NO 1
<211> LENGTH: 16
<212> TYPE: DNA
<213> ORGANISM: Artificial Sequence
<220> FEATURE:
<223> OTHER INFORMATION: 5' thiol-modified DNA oligonucleotide

<400> SEQUENCE: 1
gtgttagcct caagtg                                                    16

```
<210> SEQ ID NO 2
<211> LENGTH: 16
<212> TYPE: DNA
<213> ORGANISM: Artificial Sequence
<220> FEATURE:
<223> OTHER INFORMATION: 5' thiol-modified DNA oligonucleotide

<400> SEQUENCE: 2 tctatgcgt gaactg                                                  16

<210> SEQ ID NO 3
<211> LENGTH: 16
<212> TYPE: DNA
<213> ORGANISM: Artificial Sequence
<220> FEATURE:
<223> OTHER INFORMATION: 5' thiol-modified DNA oligonucleotide

<400> SEQUENCE: 3
gtgtatccga catgtg                                                 16

<210> SEQ ID NO 4
<211> LENGTH: 16
<212> TYPE: DNA
<213> ORGANISM: Artificial Sequence
<220> FEATURE:
<223> OTHER INFORMATION: Complement to SEQ. ID. NO: 1

<400> SEQUENCE: 4
cacttgaggc taacac                                                 16

<210> SEQ ID NO 5
<211> LENGTH: 16
<212> TYPE: DNA
<213> ORGANISM: Artificial Sequence
<220> FEATURE:
<223> OTHER INFORMATION: Complement to SEQ. ID. NO: 2

<400> SEQUENCE: 5
cagttcacgc atagac                                                 16

<210> SEQ ID NO 6
<211> LENGTH: 16
<212> TYPE: DNA
<213> ORGANISM: Artificial Sequence
<220> FEATURE:
<223> OTHER INFORMATION: Complement to SEQ. ID. NO: 3

<400> SEQUENCE: 6
cacatgtcgg atacac                                                 16

<210> SEQ ID NO 7
<211> LENGTH: 31
<212> TYPE: DNA
<213> ORGANISM: Artificial Sequence
<220> FEATURE:
<223> OTHER INFORMATION: Amino-modified DNA oligonucleotide
      (from Integrated DNA Technologies, Coralville, Iowa)

<400> SEQUENCE: 7
tttttttttt tttttgtcta tgcgtgaact g                                31

<210> SEQ ID NO 8
<211> LENGTH: 5
<212> TYPE: PRT
<213> ORGANISM: Artificial Sequence
<220> FEATURE:
<223> OTHER INFORMATION: 5-residue polypeptide linker
```

```
<400> SEQUENCE: 8

Cys Gly Ser Gly Ser
1               5
```

FUSION PROTEIN ARRAYS ON METAL SUBSTRATES FOR SURFACE PLASMON RESONANCE IMAGING

Priority is hereby claimed to provisional application Ser. No. 60/362,178, filed Mar. 6, 2002, and Ser. No. 60/304,246, filed Jul. 10, 2001, the contents of both of which are incorporated herein by reference.

FEDERAL FUNDING STATEMENT

This invention was made with United States government support awarded by the following agency: NIH GM59622. The United States has certain rights in this invention.

FIELD OF THE INVENTION

The invention is directed to methods of fabricating fusion protein arrays on metal surfaces, the arrays so formed, and a method of analyzing proteins via surface plasmon resonance.

REFERENCE CITATIONS

Complete bibliographic citations to the references described herein can be found in the Bibliography section, immediately preceding the claims. All of the references cited herein are incorporated by reference.

DESCRIPTION OF THE RELATED ART

The binding of proteins to DNA plays a pivotal role in the regulation and control of gene expression, replication and recombination. In addition, enzymes that recognize and modify specific oligonucleotide sequences are critical components of biological nucleic acid manipulation and repair systems. An enhanced understanding of how these proteins recognize certain oligonucleotide sequences would aid in the design of biomedical systems which could, for example, be used to regulate the expression of therapeutic proteins. For this reason, the study of protein-nucleic acid interactions (i.e., protein-DNA and protein-RNA interactions) is a rapidly growing area of molecular biology, aided in part by recent advances in NMR and X-ray structural determination methods. At the same time, the explosive increase in the amount of available genomic and extra-genomic (i. e., ribosomal) sequence information obtained from large-scale nucleic acid sequencing efforts creates a need to survey this vast amount of new sequence data for protein binding sites.

Simultaneously, the field of proteomics, that is, the study of interactions between large sets of diverse proteins, is experiencing explosive growth. To date, genomic research has generated a tremendous body of sequence data. However, there is currently little or no understanding of the biological significance of most of the sequence data. Translating genomic data into proteomic data and elucidating the relationships between genomics and proteomics is a far-reaching goal that will require new tools and methodologies to uncover. At present, however, the development of new tools to elucidate genetic data has far outstripped the development of new tools to elucidate protein-protein or protein-DNA interactions. Whereas "gene chips" have now become a commonplace article of commerce, the same cannot be said of "protein chips."

For example, arrays of DNA molecules attached to planar surfaces are currently employed in hybridization adsorption experiments to sequence DNA, Pease et al. (1994); to screen for genetic mutations, Winzeler et al. (1998): and in DNA computing applications, Frutos et al. (1997) and Frutos et al. (1998) (J. Am. Chem. Soc.). These arrays are exposed to solutions containing fluorescently labeled complementary DNA sequences, rinsed, and then "read-out" using fluorescence imaging methods.

The technique of surface plasmon resonance (SPR) is a surface-sensitive, optical detection method well suited to the monitoring of reversible, protein-nucleic acid interactions. The commercially successful "BIAcore" SPR instrument (Biacore AB, Uppsala, Sweden) has been used previously, for example, to study the interaction of DNA molecules with various enzymes. Although powerful, the "BIAcore" instrument has no imaging capabilities. This severely limits the number of DNA sequences that can be screened in a single experiment.

Surface plasmon resonance (SPR) is a phenomenon responsive to the thickness and index of refraction of material at the interface between a free electron metal (e.g., gold, silver, copper, cadmium, aluminum) and a bulk medium, such as air or water. Surface plasmon resonance may be achieved by using the evanescent wave which is generated when a laser beam linearly polarized parallel to the plane of incidence impinges onto a prism coated with a thin metal film. The metal may also be coated onto a thin transparent substrate such as glass, and this glass brought into optical contact with the prism. SPR is most easily observed as a reduction of the total internally reflected light just past the critical angle of the prism. This angle of minimum reflectivity (denoted as the SPR angle) shifts to higher angles as material is adsorbed onto the metal layer. The shift in the angle can be converted to a measure of the thickness of the adsorbed or added material by using complex Fresnel calculations and can be used to detect the presence or absence of materials on top of the metal layer.

In using SPR to test for biological, biochemical, or chemical substances, a beam of light from a laser source is directed through a prism onto a biosensor consisting of a transparent substrate, usually glass, which has one external surface covered with a thin film of a noble metal, which in turn is covered with an organic film that interacts strongly with an analyte, such as a biological, biochemical, or chemical substance. The organic film can contain substances (such as antibodies, antigens, DNA, RNA, etc.) which can bind with an analyte in a sample to cause an increased thickness which will shift the SPR angle. By monitoring either the position of the SPR angle or the reflectivity at a fixed angle near the SPR angle, the presence or absence of an analyte in the sample can be detected.

Various types of equipment for using SPR with a biosensor for biological or biochemical or chemical substances are described by Liedberg et al. (1983). See also European Patent Application 0 305 108 and U.S. Pat. No. 5,374,563.

The use of conventional SPR as a testing tool offers several advantages and disadvantages. For example, it is relatively fast, it requires no labeling, and it can be performed on site. However, as noted above, commercially-available devices, such as the "BIAcore" instrument, offer no imaging capabilities. Additionally, to achieve the high through-put demanded by large-scale users, there is a need for a simple, practical biosensor which can be readily modified or adapted to test a wide variety of compounds simultaneously.

In SPR imaging, a light source (typically a monochromatic, incoherent, near-infrared light source) is used to illuminate a prism/thin gold film sample assembly at an incident angle that is near the SPR angle, and the reflected light is detected at a fixed angle with a CCD camera to produce an SPR image. The SPR image arises from variations in the reflected light intensity from different parts of the sample; these variations are created by any changes in organic film thickness or index of refraction that occur upon adsorption onto the modified gold surface. Since SPR imaging is sensitive only to molecules in close proximity to the surface (within about 200 nm), unbound molecules remaining in solution do not interfere with in situ measurements.

The formation of robust, reproducible arrays of oligonucleotides tethered to metal-coated surfaces (most often gold) is an essential requirement for SPR imaging of protein-nucleic acid binding interactions. To use SPR imaging techniques, it is essential that the nucleic acid array be constructed on a noble metal surface, and for this reason DNA arrays on glass supports from commercially available sources such as Affymetrix (Santa Clara, Calif.) are not a viable option. Using self-assembled monolayers of substituted alkanethiols as a starting point, others have previously developed schemes to attach single-stranded DNA molecules to chemically modified gold surfaces. See, for example, U.S. Pat. No. 5,629,213.

Nucleic acid array technology itself has revolutionized the practice of life sciences research, providing quantitative information on complex biological systems in a fraction of the time required by traditional methods. However, the application of such technology for quantitative measurement of biomolecules has been limited by the high costs and laborious techniques associated with radioactive and fluorescent labeling and detection (Lockhart et al. (1996); Fodor (1997)). The technology also is not directly extendible to an analogous method for immobilizing proteins into a fixed array on an SPR-capable substrate.

SPR imaging has been used extensively to measure binding of biological molecules onto chemically and biologically modified surfaces, Brockman et al. (2000). SPR imaging allows multiple molecular probes to be analyzed simultaneously for affinity to a target molecule or mixtures of target molecules. Brockman et al. (1999); Nelson et al. (2001). SPR imaging has been used for the analysis of DNA hybridization, Jordan et al. (1997); Thiel et al. (1997), the detection of RNA oligonucleotide hybridization, and DNA-protein interactions, Brockman et al. (1999); Brockman et al. (2000); Frutos et al. (2000).

SPR can be coupled with the use of near-infrared (NIR) excitation. This technique results in improved image contrast and better sensitivity over the more commonly used excitation from a beam-expanded visible laser, Nelson et al. (1999). A NIR-SPR imager device uses light from a collimated white light source to illuminate a high index glass prism at a fixed angle. A gold-coated glass slide containing a nucleic acid array is optically coupled to the prism. Using UV-photopatterning techniques described by Tarlov et al. (1993), gold surfaces are chemically modified to create spatial arrays of molecules for use with SPR imaging (see U.S. Pat. No. 6,127,129). Light at 800 nm interacts with the patterned thin film from behind, creating surface plasmons. Reflectivity of the incident light is attenuated upon the creation of the surface plasmons; the momentum of these surface plasmons is determined by the index of refraction very close to the gold film. Adsorption of molecules such as nucleic acids onto the surface affects the index of refraction very close to the surface, thereby causing a change in the reflectivity of incident light. These changes in reflectivity are monitored with a CCD camera.

SUMMARY OF THE INVENTION

The present invention provides a label-free SPR-based means for analyzing proteins and protein interactions (e.g., protein-protein interactions, protein-nucleic acid interactions, etc.) By using fusion protein technology, coupled to surface attachment chemistry and surface plasmon resonance (SPR) imaging techniques, the present invention provides modified surfaces onto which have been attached biomolecules such as proteins, nucleic acids, etc. The biomolecules can be attached in any desired geometric pattern to yield biomolecule arrays on an SPR-capable substrate. These arrays are a rapid and efficient method for screening the interactions of specific biomolecules under controlled conditions.

Thus, in a first embodiment, the invention is directed to a method of immobilizing biomolecules or cells to a metal substrate, preferably an SPR-capable metal substrate. The method comprises depositing an ω-modified alkanethiol monolayer on a metal substrate, then contacting the ω-modified monolayer with a heterobifunctional compound comprising a first moiety reactive with the ω-modified alkanethiol monolayer and a second moiety comprising a protected thiol moiety. This is done under conditions wherein the heterobifunctional compound binds to the ω-modified alkanethiol monolayer via the first moiety. The second moiety of the heterobifunctional compound is then deprotected to yield an unprotected thiol moiety. A biomolecule or cell is then attached to the unprotected thiol moiety. In this fashion, the biomolecule or cell is immobilized to the metal substrate.

A second embodiment of the invention utilizes the same technique described in the immediately preceding paragraph to make biomolecule or cellular arrays on a metal substrate. Here, the method comprises first depositing an alkanethiol monolayer on a metal substrate, and then removing the alkanethiol monolayer from the substrate at discrete areas to create an array of exposed metal substrate areas. Preferably, this is done by selectively exposing the monolayer to UV radiation. Into the areas of exposed metal substrate is deposited ω-modified alkanethiol, thereby yielding an array of discrete, unprotected ω-modified alkanethiol spots. The discrete, unprotected ω-modified alkanethiol spots are then contacted with a heterobifunctional compound comprising a first moiety reactive with the ω-modified alkanethiol spots and a second moiety comprising a protected thiol moiety. As in the first embodiment, this is done under conditions wherein the heterobifunctional compound binds to the ω-modified alkanethiol spots via the first moiety. The second moiety of the heterobifunctional compound is then deprotected to yield an array of unprotected thiol moieties. Biomolecules or cells are then attached to the array of unprotected thiol moieties, thereby yielding a biomolecule or cellular array on the metal substrate.

A third embodiment of the invention is also a method of immobilizing biomolecules or cells to a metal substrate. This embodiment, however, utilizes a disulfide bond to immobilize the biomolecule or cell to the substrate. The first three steps proceed as outlined above for the first embodiment, to the point where the second moiety of the heterobifunctional compound is deprotected to yield an unprotected thiol moiety. At this point, in the third embodiment, the unprotected thiol moiety is reacted with a disulfide-containing compound under conditions wherein the disulfide-containing compound undergoes a thiol-disulfide exchange reaction with the unprotected thiol moiety. This converts the unprotected thiol moiety into a disulfide link. The disulfide link is then reacted with a thiol-containing biomolecule or cell, which results in the biomolecule or cell being immobilized on the metal substrate via a disulfide link.

A fourth embodiment of the invention utilizes the chemistry described in the preceding paragraph to make a biomolecule or cellular array on a metal substrate. This embodiment comprises first depositing an alkanethiol monolayer on a metal substrate and then removing the alkanethiol monolayer from the substrate at discrete areas to create an array of exposed metal substrate areas. Into the areas of exposed metal substrate is then deposited ω-modified alkanethiol, thereby yielding an array of discrete, unprotected ω-modified alkanethiol spots. The discrete, unprotected ω-modified alkanethiol spots are then contacted with a heterobifunctional compound comprising a first moiety reactive with the ω-modified alkanethiol spots and a second moiety comprising a protected thiol moiety (under conditions wherein the heterobifunctional compound binds to the ω-modified alkanethiol spots via the first moiety) The second moiety of the heterobifunctional compound is then deprotected to yield an array of unprotected thiol moieties. At this point, the unprotected thiol moieties are contacted with a disulfide-containing compound under conditions wherein the disulfide-containing compound undergoes a thiol-disulfide exchange reaction with the unprotected thiol moieties, thus converting the unprotected thiol moieties into disulfide links. Thiol-containing biomolecules or cells are then reacted with the disulfide links created in the preceding step, thereby yielding a biomolecule or cellular array on the metal substrate.

A fifth embodiment of the invention is directed to a method of immobilizing biomolecules, preferably proteins, to a metal substrate. This embodiment of the invention comprises first depositing an ω-modified alkanethiol monolayer on a metal substrate and then contacting the ω-modified monolayer with a heterobifunctional compound. The heterobifunctional compound comprises two reactive moieties: a first moiety reactive with the ω-modified alkanethiol monolayer and a second moiety comprising a protected thiol moiety. The heterobifunctional compound is contacted with the ω-modified monolayer under conditions wherein the heterobifunctional compound binds to the ω-modified alkanethiol monolayer via the first moiety. The second moiety of the heterobifunctional compound is then deprotected to yield an unprotected thiol moiety. Then, a glutathione-containing molecule bonded to the unprotected thiol moiety, thereby anchoring the glutathione-containing molecule to the substrate. A GST-containing molecule is then contacted to the glutathione-containing molecule, whereby the GST-containing molecule is reversibly adhered to the glutathione-containing molecule. In the preferred approach, the GST-containing molecule is a GST fusion protein.

An analogous sixth embodiment of the present invention utilized the chemistry described in the preceding paragraph to make a biomolecule array on a metal substrate. The array is constructed by first depositing an alkanethiol monolayer on a metal substrate and then removing the alkanethiol monolayer from the substrate at discrete areas to create an array of exposed metal substrate areas. Again, the preferred method for removing the monolayer is by selective exposure to UV radiation. Into the areas of exposed metal substrate is then depositing ω-modified alkanethiol, thereby yielding an array of discrete, unprotected ω-modified alkanethiol spots. The discrete, unprotected ω-modified alkanethiol spots are then contacted with a heterobifunctional compound comprising a first moiety reactive with the ω-modified alkanethiol spots and a second moiety comprising a protected thiol moiety, under conditions wherein the heterobifunctional compound binds to the ω-modified alkanethiol spots via the first moiety. The second moiety of the heterobifunctional compound is then deprotected to yield an array of unprotected thiol moieties. Glutathione-containing molecules are then attached to the array of unprotected thiol moieties, thereby yielding an array of glutathione-containing molecules on the metal substrate. Lastly, GST-containing molecules are contacted to the glutathione-containing molecules of the preceding step, whereby the GST-containing molecules are reversibly adhered to the glutathione-containing molecules. It is preferred that the GST-containing molecules are GST fusion proteins.

A seventh embodiment of the invention is directed to a method of immobilizing a biomolecule to a metal substrate, the method comprising first depositing an ω-modified alkanethiol monolayer on a metal substrate and then contacting the ω-modified monolayer with a heterobifunctional compound comprising a first moiety reactive with the ω-modified alkanethiol monolayer and a second moiety comprising a protected thiol moiety, under conditions wherein the heterobifunctional compound binds to the ω-modified alkanethiol monolayer via the first moiety. The second moiety of the heterobifunctional compound is then deprotected to yield an unprotected thiol moiety. The unprotected thiol moiety is then contacted with a disulfide-containing compound under conditions wherein the disulfide-containing compound undergoes a thiol-disulfide exchange reaction with the unprotected thiol moiety, whereby the unprotected thiol moiety is converted into a disulfide link. A glutathione-containing molecule is then reacted with the disulfide link created in the preceding step, whereby the glutathione-containing molecule is immobilized on the metal substrate. Lastly, a GST-containing molecule is contacted to the glutathione-containing molecule, whereby the GST-containing molecule is reversibly adhered to the glutathione-containing molecule.

An eight embodiment of the invention utilizes the approach described in the preceding paragraph to make a biomolecule array on a metal substrate. The array is fabricated by first depositing an alkanethiol monolayer on a metal substrate and then removing the alkanethiol monolayer from the substrate at discrete areas to create an array of exposed metal substrate areas. An ω-modified alkanethiol is then deposited in the areas of exposed metal substrate, thereby yielding an array of discrete, unprotected ω-modified alkanethiol spots. The discrete, unprotected ω-modified alkanethiol spots are then contacted with a heterobifunctional compound comprising a first moiety reactive with the ω-modified alkanethiol spots and a second moiety comprising a protected thiol moiety, under conditions wherein the heterobifunctional compound binds to the ω-modified alkanethiol spots via the first moiety. The second moiety of the heterobifunctional compound is then deprotected to yield an array of unprotected thiol moieties. The unprotected thiol moieties are then contacted with a disulfide-containing compound under conditions wherein the disulfide-containing compound undergoes a thiol-disulfide exchange reaction with the unprotected thiol moieties, whereby the unprotected thiol moieties are converted into disulfide links. Glutathione-containing molecules are then contacted with the disulfide links created in the preceding step, whereby the glutathione-containing molecules are immobilized on the metal substrate. Lastly, GST-containing molecules are contacted to the glutathione-containing molecules from the previous step, whereby the GST-containing molecules are reversibly adhered to the glutathione-containing molecules.

The invention also encompasses a composition of matter or array fabricated according to any of the above-described methods. Thus, the invention also encompasses, for example, a composition of matter comprising: a metal substrate; an ω-modified alkanethiol monolayer adhered to the metal substrate; a heterobifunctional compound comprising a first moiety reactive with the ω-modified alkanethiol monolayer and a second moiety comprising a thiol moiety, wherein the heterobifunctional compound is bonded to the ω-modified alkanethiol monolayer via the first moiety; a glutathione-containing molecule bonded to the thiol moiety of the heterobifunctional compound; and a GST-containing biomolecule adhered to the glutathione-containing molecule, whereby the GST-containing biomolecule is reversibly adhered to the glutathione-containing molecule. Likewise, the invention encompasses a composition of matter comprising: a metal substrate; an ω-modified alkanethiol monolayer adhered to the metal substrate; a heterobifunctional compound comprising a first moiety reactive with the ω-modified alkanethiol monolayer and a second moiety comprising a sulfur atom capable of forming a disulfide bond, wherein the heterobifunctional compound is bonded to the ω-modified alkanethiol monolayer via the first moiety; a glutathione-containing molecule bonded to the sulfur atom of the heterobifunctional compound via a disulfide link; and a GST-containing biomolecule adhered to the glutathione-containing molecule, whereby the GST-containing biomolecule is reversibly adhered to the glutathione-containing molecule. In these compositions of matter, it is preferred that the GST-containing biomolecule is a GST fusion protein.

The methods, compositions of matter, and arrays described herein are useful for the SPR analysis of biomolecules and cells in general, and in particular for the SPR analysis of polypeptides, proteins, and nucleic acids.

BRIEF DESCRIPTION OF THE DRAWINGS

FIG. 5A is the difference image before and after introduction of complementary DNA (SEQ. ID. NO: 4) to the surface. FIG. 5B is the difference image after denaturing the surface with 8 M urea and introduction of complementary DNA (SEQ. ID. NO: 5). Thiol DNA sequences were spotted on the array as shown in the FIG. legend.

DETAILED DESCRIPTION OF THE INVENTION

Figure 1:
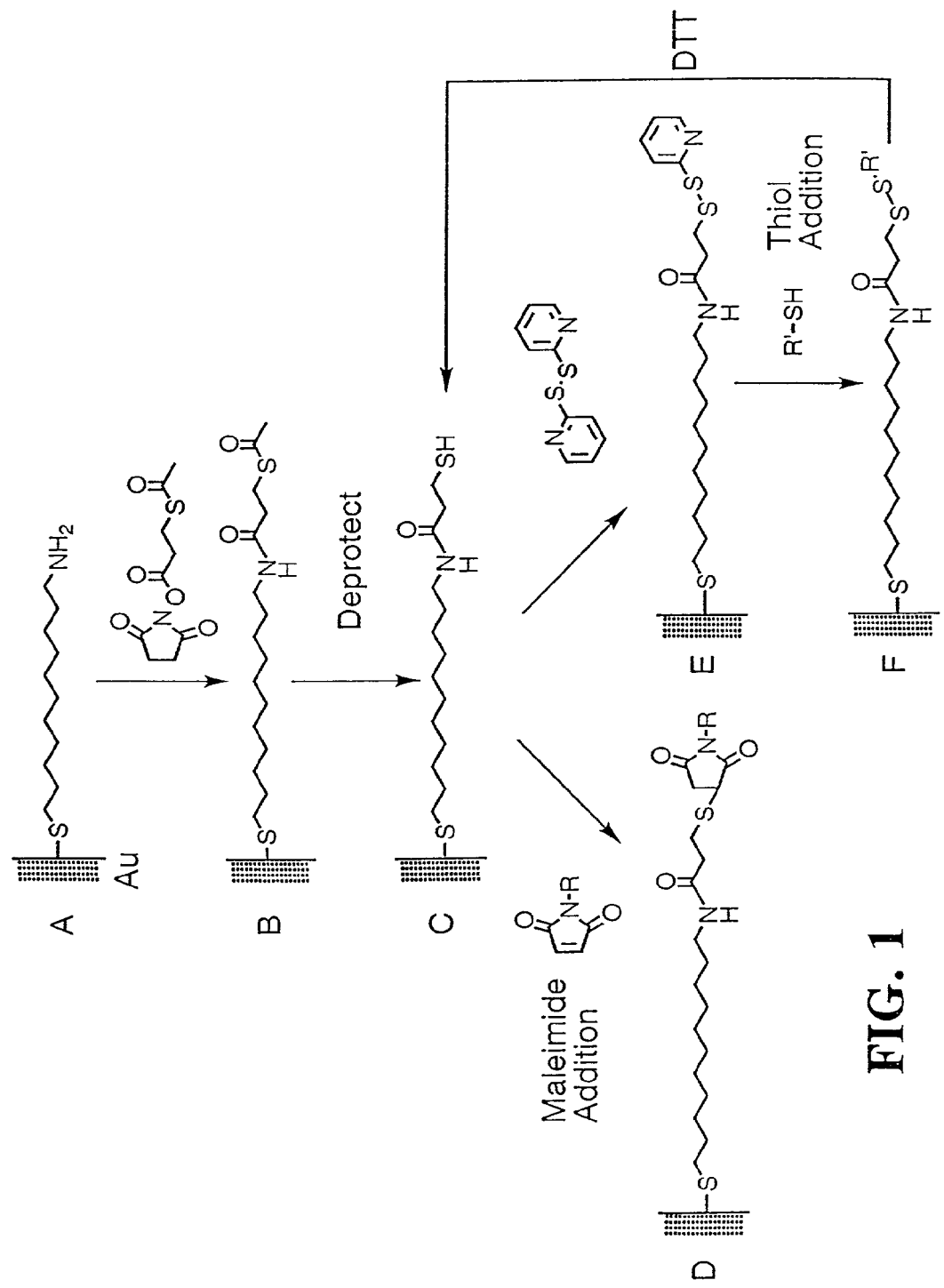
FIG. 1 is a schematic of the subject surface attachment method using SATP: (A) MUAM surface; (B) thiolation with SATP; (C) sulfhydryl deprotection; (D) reaction of the sulfhydryl surface with maleimide derivatives (N-ethyl maleimide and maleimide-modified DNA); (E) activated sulfhydryl surface with pyridyl groups; (F) exchange reactions between the pyridyl disulfide surface and sulfhydryl-containing molecules (R'—SH) in solution, thereby producing a leaving group, pyridine-2-thione. When surface (F) is exposed to DTT, the disulfide linkage is broken, thereby releasing the immobilized molecule and regenerating the free sulfhydryl surface (C).

Abbreviations and Commercial Suppliers:

The following abbreviations and terms are used throughout the specification and claims. All other terms have their standard, accepted meaning in the relevant art.

"AEBSF"=4-(2-aminoethyl)benzenesulfonyl fluoride.

"biomolecule"=any molecule found in biological material, expressly including, but not limited to nucleic acids, proteins, peptides, antibodies, enzymes, cell-wall components such as phospholipids, etc., and modified and synthetic forms thereof, such as labeled biomolecules and recombinant biomolecules.

"BSA"=bovine serum albumin (Sigma Chemical Co., St. Louis, Mo.).

"DMF"=N,N-dimethylformamide.

"DPDS"=2,2-dipyridyl disulfide

"DTT"=dithiothreitol. p1 "EDTA"= ethylenediaminetetraacetic acid disodium salt dihydrate.

"Fmoc-NHS"=9-fluorenylmethoxycarbonyl-N-hydroxysuccinimide (Novabiochem, La Jolla, Calif.).

"GSH"=glutathione.

"GST"=glutathione-S-transferase.

"metal substrate" or "metal film"=a metal thin film of gold, silver, copper, nickel, platinum, palladium, rhodium, titanium, and the like. Gold is preferred.

"MUAM"=11-mercaptoundecylamine.

"NHSS"=N-hydroxysulfosuccinimide ester.

"nucleic acids"=deoxyribonucleic acids (DNA), ribonucleic acids (RNA), and peptide nucleic acids from any source, and modified forms thereof, including, without limitation, labeled (radioactive, fluorescent, etc.) nucleic acids, and nucleic acids modified to include a binding moiety such as a thiol group or a biotin tag.

"ODT"=1-octadecanethiol.

"PEG"=poly(ethylene glycol).

"PEG-NHS"=N-hydroxysuccinimidyl ester of methoxypoly(ethylene glycol) propionic acid MW 2000 (Shearwater Polymers, Inc., Huntsville, Ala.).

"PMDS"=polydimethylsiloxane.

"PM-FTIRRAS"=Polarization modulation Fourier transform infrared reflection-absorption spectroscopy.

"poly(ethylene glycol)-modified alkanethiol"=$HS(CH_2)_{11}(OCH_2CH_2)_3OH$.

"SATP"=N-succinimidyl-5-acetylthiopropionate.

"SDS"=sodium dodecylsulfate.

"SPR"=surface plasmon resonance.

"SSB"=single-stranded DNA binding protein (Pharmacia Biotech, Piscataway, N.J.).

"SSMCC"=sulfosuccinimidyl4-(N-maleimidomethyl)cyclohexane-1-carboxylate (Pierce Chemical, Rockford, Ill.).

"SSPE"=An aqueous buffer containing NaCl, $NaH_2PO_4$, and EDTA.

"TAEA"=tris(2-aminoethyl)amine (Aldrich Chemical Co., Milwaukee, Wis.).

"TEA"=triethanolamine hydrochloride (Sigma)

"ω-modified alkanethiol"=an alkanethiol whose terminal carbon atom has been modified by the addition of a chemically-reactive moiety such as an amino, hydroxy, carboxy, or thiol moiety.

The above chemicals and were all used as received. Solvents were of standard laboratory grade and Millipore (Marlborough, Mass.) filtered water was used for all aqueous solutions and rinsing.

As noted above, a first embodiment of the invention is directed to a method for creating biomolecule arrays, and specifically protein arrays, on chemically-modified metal At substrates. It is much preferred, although not required, that these substrates be SPR-capable substrates, meaning that the substrates can be analyzed via surface plasmon resonance techniques. The arrays created using the present methods, however, can also be analyzed by other means, thus it is not required that the arrays be formed on an SPR-capable substrate. These arrays are used in the study of biological and/or chemical interactions involving biomolecules, including protein-protein and protein-DNA interactions, preferably using SPR. Thus, the method and the resulting arrays described herein find use in elucidating the reactions of proteins, nucleotides, and other biomolecules.

For sake of expository brevity only, the discussion that follows is limited to a description of fabricating protein arrays and DNA arrays on a modified metal surface using the inventive method. The methods will, however, function to immobilize any type of molecule that contains or can be modified to contain a maleimide moiety, a thiol group, or a GST tag.

There are several obstacles that hinder the use of traditional high-throughput surface-based techniques, widely used in genomic analysis, for analysis of proteins. For example, many proteins adhere to surfaces non-specifically, or lose their bioactivity upon becoming adhered to a surface. To solve this problem, it is necessary to fabricate a surface that simultaneously: 1) minimizes or eliminates non-specific protein adsorption at given locations; 2) uses robust chemical attachment strategies at other locations to immobilize proteins firmly to the surface; and 3) firmly immobilizes the protein to the surface without adversely affecting the bioactivity of the immobilized protein. The present invention satisfies all three of these requirements.

Figure 6:
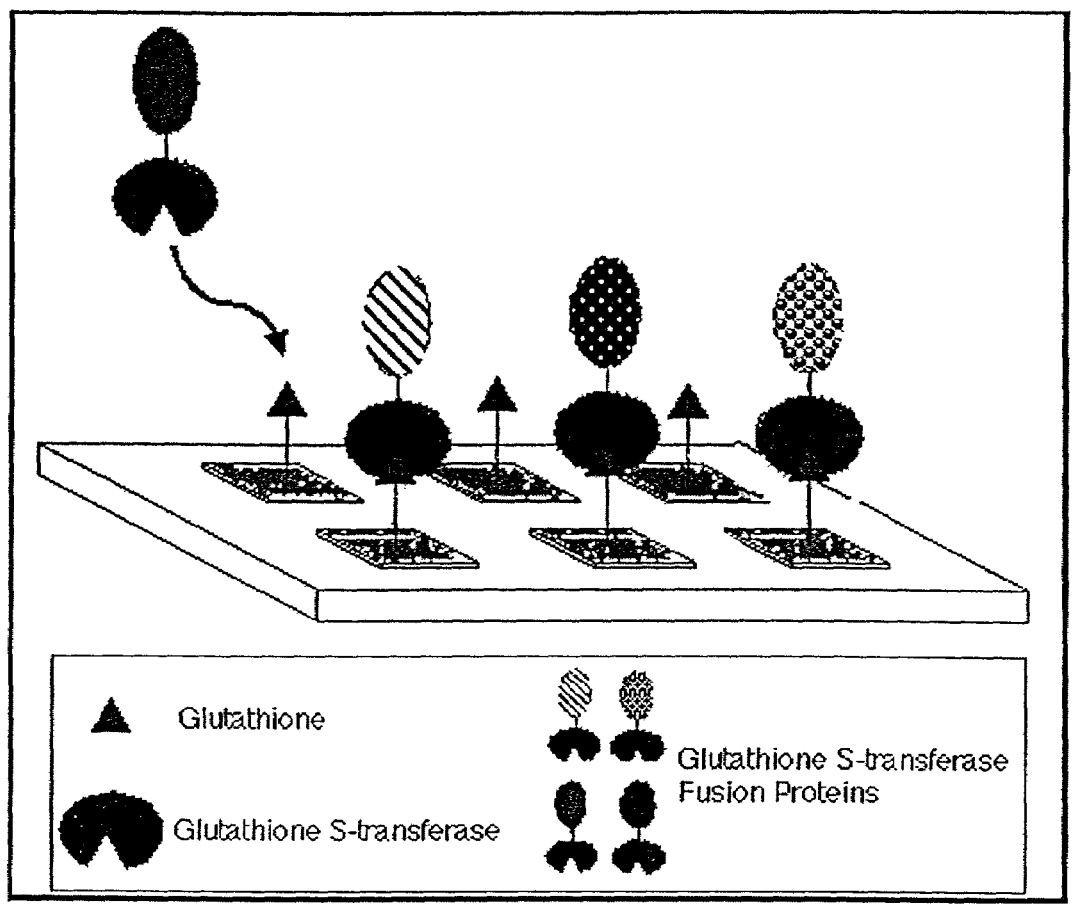
FIG. 6 is a schematic illustrating the fabrication of protein arrays using discrete GSH domains immobilized on an SPR-capable substrate and immobilizing GST fusion proteins to the GSH domains.

Specifically, in the preferred embodiment of the invention, the interaction of the protein glutathione-S-transferase (GST) and the tripeptide glutathione (GSH) (γ-glutamic acid, cysteine, glycine) is utilized to adhere proteins to a metal substrate. The general approach is illustrate schematically in FIG. 6.

In the first step, a GSH array is created on a modified metal substrate (preferably a gold substrate). The array comprises discrete domains of GSH attached (indirectly) to the metal surface via (preferably) a disulfide linking reaction between the cysteine of GSH and a thiol-terminated self-assembled monolayer on the metal substrate. As shown in the FIG. 6, the discrete domains are squares roughly 500 μm per side. The geometry, however, of the discrete domains is not critical to the functionality of the invention and the discrete domains can take any shape whatsoever (regular or irregular polygons, circles, ovals, lines, circumscribed or inscribed patterns, etc.). See the discussion that follows and the Examples for a detailed description of how the thiol-terminated monolayer is formed. The background (i.e., the areas of the substrate not covered by a discrete GSH domain) are made resistant to non-specific protein binding. This is accomplished by attaching polyethylene glycol moieties to the background.

A linker moiety may be disposed between the GSH to be immobilized on the substrate surface and the thiol-terminated self-assembled monolayer. Thus, for example, a polypeptide linker may be interposed between the GSH and the thiol-terminated monolayer. A cysteine-terminated polypeptide linker is preferred because the thiol moiety within the cysteine residue can be utilized in forming the disulfide attachment described hereinbelow. For example, a 5-residue linker, Cys-Gly-Ser-Gly-Ser (SEQ. ID. NO: 8), is particularly useful:

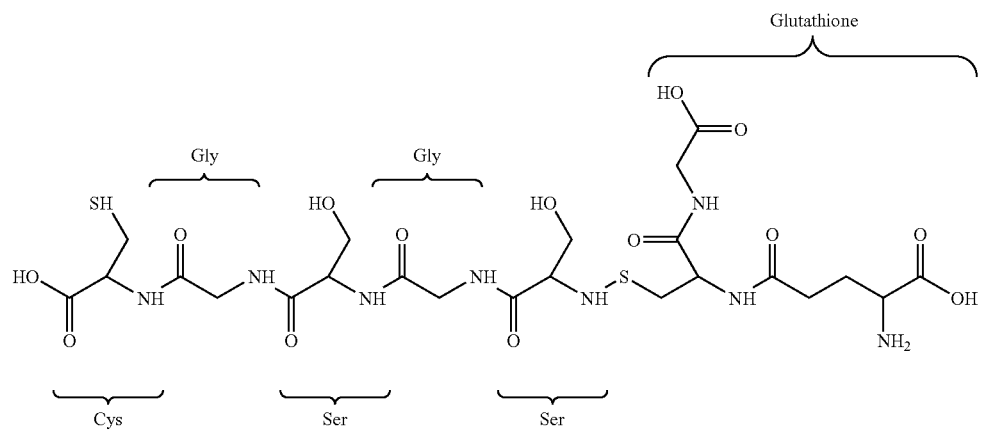

Other linkers, preferably having from 1 to 12 atoms in the backbone, can be utilized in the invention, such as thiol-terminated $C_1$–$C_{12}$ alkanes.

After the GSH array is formed, the specific binding between GSH and GST is then used to immobilize GST fusion proteins onto the modified metal substrate. Via a non-covalent, but highly specific reaction with the immobilized GSH, the GST portion of the fusion protein acts as an anchor to immobilize the fusion protein to the surface. Simultaneously, the remainder of the protein remains accessible for interaction studies with literally any other type of chemical, including (without limitation) peptides, proteins, nucleotides, or small molecules (organic or inorganic).

The interaction between GSH and GST is known but is conventionally employed in a bead column format for the purification of proteins. See, for example, Simons & Vander Jagt (1977) and Toribio et al. (1996). The GSH/GST interaction, however, has never before been utilized in SPR imaging.

Creating GST fusion proteins is a straightforward process and GST fusion protein kits are available from a number of commercial suppliers, such as Novagen, Madison, Wis. (See the pET GST Fusion Systems 41 and 24, catalog nos. 70559 and 70564, respectively, and Novagen Technical Bulletin TB055, $9^{th}$ Edition, May 2000). See also U.S. Pat. No. 5,654,176. Functionally identical kits for making GST fusion proteins are also sold by Chemicon International, Inc., Temecula, Calif., and Invitrogen/Life Technologies, Carlsbad, Calif. See, for example, Life Technologies' instruction manual for its "GATEWAY"—brand cloning technology (vectors pDEST15, pDEST27, and pDEST20 are designed specifically for producing N-terminal GST fusion proteins in *E. coli*, mammalian cells, and baculovirus, respectively).

As a general proposition, the commercial GST gene fusion systems are integrated kits that contain all of the necessary reagents for expressing, purifying, and detecting GST fusion proteins produced in bacterial, yeast, mammalian, and/or insect cells. The sequence encoding the GST protein is incorporated into an expression vector, generally upstream of a multi-cloning site. The sequence encoding the protein of interest is then cloned into this vector. Induction of the vector into a host cell system thus results in expression of a fusion protein—that is, the protein of interest fused to the GST protein. The GST portion of the fusion is situated at the N-terminus of the protein of interest. The fusion protein can then be released from the cells and purified.

As noted above, purifying the fusion protein is facilitated by the affinity of the GST portion of the fusion protein for GSH. Thus, in the commercial kits, GSH molecules are coupled to an inert resin and the expressed fusion protein product is brought into contact with the GSH-coated resin. The fusion protein will bind to the GSH-coated resin and all other non-specific proteins can then be rinsed from the resin. The fusion protein can then be released from the resin by using a buffer containing a high concentration of glutathione (preferred), or by heating gently, or by using a mild elution buffer having a low pH. In the present invention, the fusion proteins would be utilized at this point in the process. That is, the present method utilizes the entire GST fusion protein, taking advantage of the GST portion's affinity for GSH to provide specific binding of the fusion protein to the modified metal surface.

It should be noted, however, that it is possible to remove the GST from the fusion protein (thereby generating the native protein of interest, absent the GST "tag") by using a number of different enzymes, including thrombin and factor X. These enzymes cleave specific sites between the GST portion of the fusion protein and the remainder of the protein chain. This is a beneficial aspect of the present invention because not only can the method and arrays be used to identify and characterize biological interactions of interest, the method also allows the chemical species involved in the interaction to be isolated free of the GST tag.

Fusion proteins can also be detected easily using anti-GST antibodies. Anti-GST antibodies can be purchased commercially from many sources (e.g., PanVera, Madison, Wis.).

The commercially available GST systems have a number of advantages that make them very convenient "all-purpose" tools for making GST fusion proteins. Most notably, the GST expression systems are truly generic tools for protein expression, purification, and detection. There is no need to produce individual antibodies to each protein of interest. Suitable GST expression vectors are available for use in all expression systems, including bacterial, yeast, mammalian, and baculovirus hosts. These vectors encode cleavage sites to allow the GST portion of the fusion to be removed from the protein of interest. The GSH-immobilized purification resins are quite inexpensive and can be regenerated for multiple uses. The purification process is very simple and straightforward and uses very mild elution conditions, thus leaving the protein with its biological activity intact. The purity of the resulting protein is also quite high. In short, these GST fusion systems are widely used in the art and are well known to those skilled in the art.

Moreover, many recent papers have shown that GST fusion proteins can be expressed in host bacteria and that these proteins retain their biological activity when attached to a solid support such a dextran films or agarose beads. See Harboth et al. (2000); Youtani et al. (2000); Lin et al. (2000); Quetglas et al. (2000); Herzog et al. (2000); Gokce et al. (2000); and Martzen et al. (1999).

A typical protocol for isolating a GST fusion protein from a yeast host proceeds as follows:

Using 2.5 ml of an overnight culture of the GST-transformed yeast in a suitable medium, inoculate a 50 ml portion of new medium and grow at 30° C. with shaking until $OD_{600}$=0.8 to 1.2. Add 1 M $NaN_3$ to a final concentration of 10 mM and move cultures to ice. All subsequent steps should proceed on ice. Measure $OD_{600}$ and adjust volume to give an $OD_{600}$ of about 30.

Spin the cells at 2000×g for 10 min. at 4° C., and resuspend them in 2 ml of cold 10 mM $NaN_3$. Split the samples into two 1 ml samples. Wash the samples with 1 ml lysis buffer (cold) (40 mM TEA, 2 mM EDTA, 150 mM NaCl, 2 mM DTT, 0.2 mM AEBSF 15 µg/ml leupeptin, 20 µl pepstatin, 1 mM benzamidine, 10 µg/ml aprotinin, 100 µM β-glycerolphosphate, and 0.5 mM Na—O-vanadate). Centrifuge again for 10 min. at 4° C. and resuspend in 400 µl lysis buffer. If different lysis conditions are being used, each of the two samples from the preceding step should washed and resuspended with the appropriate lysis buffer.

Add glass beads to the samples and vortex for 1 min, 4 times. The samples should be kept cold between vortexing.

Poke a hole in the bottom of the microfuge tube and spin the lysed cell mix into a new microfuge tube (500×g, 10 min., 4° C.). Transfer the liquid from the bottom tube into a new microfuge tube. Centrifuge the sample again (500×g, 10 min., 4° C.) and transfer the liquid into a new microfuge tube.

Add Triton X-100 to 1 % and mix for 60 min. at 4° C. Centrifuge at 1000×g for 10 min. at 40° C.). Remove 30 µl of liquid and add 30 µl 2×SDS PAGE sample buffer. This aliquot will measure protein content prior to glutathione purification.

To the remaining liquid, add 100 µl of a 20–30% slurry of glutathione beads and mix at 4° C. for 2 to 3 hours. The GSH beads should be prewashed three times with PBS and once with the lysis buffer before resuspending the beads as a 20–30% slurry in the lysis buffer.

Then wash the GSH beads three times with PBS at room temperature. Resuspend the beads in SDS-PAGE sample buffer. Heat the resuspended beads to 100° C. for 10 min. Then store at −20° C. The fusion protein is now ready to be run on a standard SDS-PAGE gel for isolation. The fusion protein can also be separated from the beads using the separation buffers that are supplied in the commercial kits.

The fusion proteins so generated can then be adhered specifically to the discrete GSH domains on the modified metal substrate simply by contacting the modified metal substrate with a solution containing the fusion protein and then rinsing the substrate. The GST portion of the fusion proteins binds specifically with the discrete GSH domains, thereby yielding an array of proteins firmly immobilized in discrete domains on an SPR-capable metal substrate.

SPR imaging is then used to detect the interactions of the fusion protein array with other molecules in solution. Most of the traditional methods used in the study of protein-protein interactions involve the use of radioactive or fluorescent tags. Use of either type of tag is an expensive and time-consuming process. SPR, in contrast, is label-free, requiring neither radioactive, fluorophoric, nor chromophoric tags.

Figure 7:
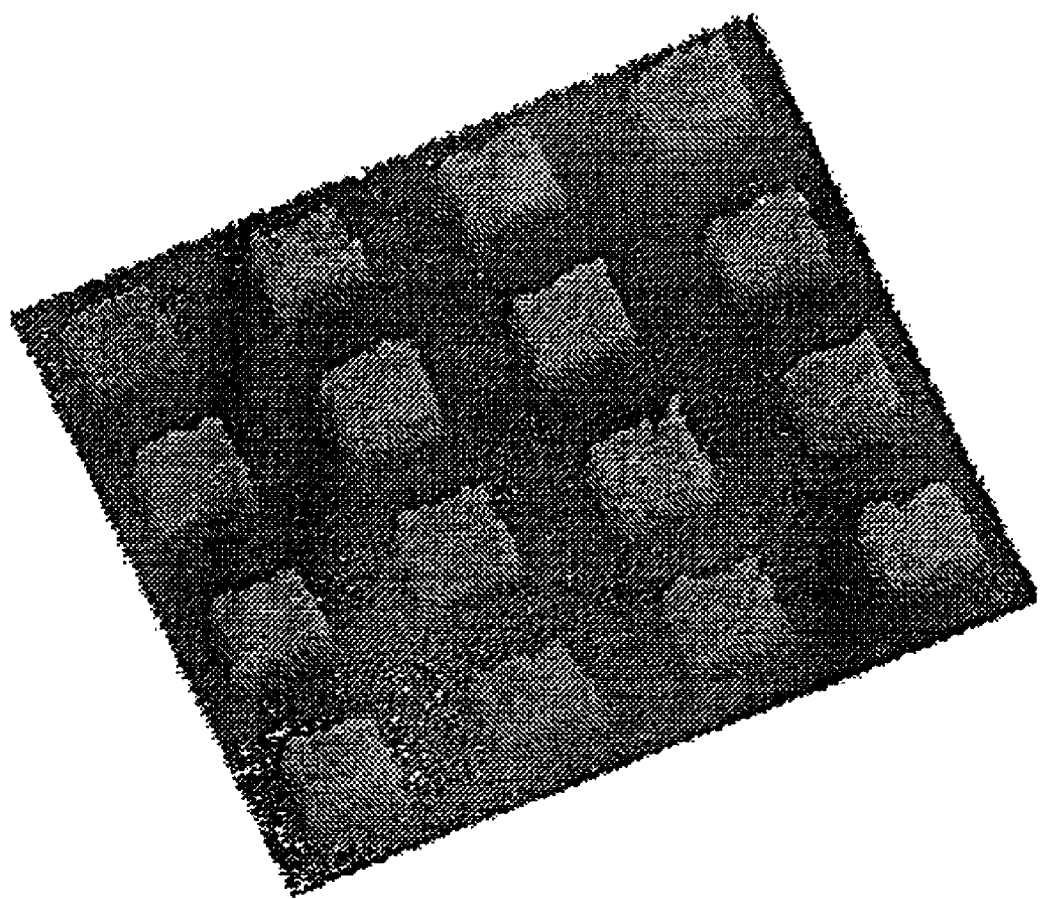
FIG. 7 is an SPR image of a protein array fabricated by the method illustrated schematically in FIG. 6

FIG. 7, for example, depicts a SPR difference image obtained by subtracting the images of a GSH array before and after exposing it to a solution containing 500 nM of GST-VanR fusion protein. The fusion protein was made by conventional methods, as described herein. The VanR protein itself is a bacterial response regulator protein that plays a role in the vancomycin resistance exhibited by certain strains of *Enterococcus faecium* (such as ATCC 51575). See, for example, Arthur, Molinas, & Courvalin (1992). The image of FIG. 7 clearly shows that the protein binds to the GSH array elements. Addition of a solution containing excess glutathione can be used to competitively wash the bound protein from the GSH-patterned portions of the substrate (results not shown), thereby demonstrating that the GST fusion protein is specifically interacting with the GSH domains immobilized on the substrate.

The chemical modification of a metal substrate to create a surface plasmon resonance-capable nucleic acid array thereon proceeds as described in U.S. Pat. No. 6,127,129, issued Oct. 3, 2000, and incorporated herein by reference. Briefly, these steps proceed as follows:

(1). Self-assembly of an ω-modified alkanethiol monolayer on a metal substrate. The ω-modification to the alkanethiol may be the addition of any moiety with enables further covalent linkages to be made the ω-terminus of the alkanethiol. Such modifications include, without limitation, the addition of an amine group, a hydroxyl group, a carboxyl group, or a thiol group to the ω carbon of the alkanethiol chain. The alkanethiol monolayer is preferably an amino-$C_8$–$C_{24}$-alkanethiol, a straight-chain alkane being much preferred to branched alkane; the most preferred ω-modified alkanethiol is MUAM.

(2). Reaction of the ω-modified alkanethiol surface with a hydrophobic protecting group, most preferably Fmoc.

(3). Photopatterning of the surface to create an array of bare metal areas.

(4). Re-assembly using additional ω-modified alkanethiol to fill in the bare metal array elements, thereby yielding islands of ω-modified alkanethiol.

(5). Covalently attaching biomolecules or cells to the islands of ω-modified alkanethiol.

(6). Removal of the protecting group from the array background.

(7). Reaction of the background with a material, preferably PEG, to make the background resistant to non-specific protein binding.

To ensure the quality of the finished product, each of the above steps may be monitored using PM-FTIRRAS, contact angle measurements, and scanning-angle SPR.

The above steps are now described in greater detail:

Step (1). In step (1), a monolayer of ω-modified alkanethiol, preferably an amine-terminated alkanethiol, most preferably MUAM, is self-assembled from an ethanolic solution onto a silanized substrate (glass or other substrate transparent to the wavelengths of radiation to be used in subsequent analysis) coated with a thin noble-metal film. A substrate (e.g., glass) coated with a very thin layer of chromium (about 1 nm) is equally suitable. In the preferred embodiment, a film of gold about 450 Å thick is used. The thickness of the metal film is not overly critical insofar as the film is uniformly applied and will function in SPR imaging analysis. Self-assembled monolayers of ω-modified alkanethiols on gold have been described previously, see, for example, Thomas et al. (1995), and are generally accepted by most to form well-ordered, mono-molecular films. However, if left exposed for extended periods of time, the terminal amine groups of amino-modified alkanthiols will react with $CO_2$ to form carbamate salts on the surface. Consequently, amino-terminated alkanethiol-coated substrates should be handled with care and their exposure to $CO_2$ minimized.

Step (2). In step (2) of the array fabrication, the MUAM covered surface is reacted with a reversible protecting group to create a hydrophobic surface. In the case of MUAM, an amine-modified alkanethiol, the protecting group is, appropriately, an amino protecting group, preferably Fmoc. Fmoc is a bulky, hydrophobic, base labile, amine protecting group routinely used in the solid phase synthesis of peptides. The choice of protecting group used is dependent in large measure upon the nature of the ω-modification made to the alkanethiol. If the ω-modification is the addition of a carboxyl group, a hydrophobic carboxy-reactive protecting group would be used. Likewise, if the ω-modification is the addition of a hydroxyl or thiol group, a hydrophobic hydroxy-reactive or thiol-reactive protecting group, respectively, would be used. Any type of hydrophobic protecting suitable for protecting the ω-modification used on the alkanethiol can be utilized in the present invention. Numerous such protecting groups, for any number of reactive moieties, such as amine, hydroxy, and carboxy functionalities, are known to the art. For example, chloride derivatives of both Fmoc and trityl to can be used to reversibly modify hydroxyl-terminated alkanethiols.

When using Fmoc, the N-hydroxysuccinimide ester of Fmoc (Fmoc-NHS) reacts with the terminal amine moiety of the MUAM molecule to form a stable carbamate (urethane) linkage, covalently attaching the Fmoc group to the surface. After reaction 25 with Fmoc-NHS, the surface properties of the array are changed significantly; the surface is extremely hydrophobic as confirmed by the measured contact angle of 74.4°±2.5°. In addition, an increase in the film thickness to 22.8 Å±0.5 Å is measured with scanning angle SPR.

Step (3). In step (3) the bond anchoring the ω-modified alkanethiol to the metal substrate is selectively cleaved to yield a patterned surface of exposed metal. UV photopatterning is preferred to create the patterned surface, although the means to create the patterned surface is not critical so long as the method yields the desired pattern. For example, micro-contact printing methods can also be used to yield a patterned surface. Using UV patterning, the surface is exposed through a quartz mask to UV radiation which photo-oxidizes the gold-sulfur bond that anchors the alkanethiol monolayers to the surface. The surface is then rinsed, removing the photo-oxidized alkanethiol and leaving an array of bare metal pads surrounded by a hydrophobic MUAM+Fmoc background.

Step (4). In step (4), the surface is again exposed to an ω-modified alkanethiol solution (in the preferred embodiment an ethanolic solution of MUAM) whereby the alkanethiol assembles into the bare gold regions producing a surface composed of hydrophilic MUAM pads surrounded by the hydrophobic Fmoc background. This difference in hydrophobicity between the reactive MUAM regions and the background is essential for the pinning of small volumes of aqueous biomolecule or cell solutions onto individual array locations.

Step (5). In step (5) in the process, biomolecules or cells (preferably nucleic acids, and more preferably still, DNA) are then covalently attached to the surface. The MUAM reactive pads are first exposed to a solution of a bifunctional linker. The linker must be capable of binding at one end to the ω-modified alkanethiol surface and at the other end to the biomolecule or cell to be immobilized to form the desired array. Any bifunctional linker having these characteristics can be used in the present invention. The preferred bifunctional linker is SSMCC, a heterobifunctional linker which contains both an N-hydroxysulfosuccinimide (NHSS) ester and a maleimide functionality. The NHSS ester end of the molecule reacts with the free amine groups on an amino-modified surface, such as the MUAM spots, creating pads terminated in maleimide groups which are reactive towards thiol. Small volumes (40 to 100 nL) of 1 mM solutions of 5'-thiol-modified DNA sequences are then spotted at discrete array locations and react to form a covalent attachment to the surface. Using this technique, a whole host of biomolecules (DNA, RNA, proteins, lipids, etc.) and/or whole cells can be spotted at different array locations.

A variation on this attachment scheme whereby thiol-DNA is linked via SSMCC to a MUA/PL (11-mercaptoundecanoic acid/poly-L-lysine) bilayer has been used quite extensively, see U.S. Pat. No. 5,629,213. Other researchers have used the direct self-assembly of thiol-terminated DNA molecules on gold to prepare functionalized surfaces, but this method has the disadvantage that only weak forces exist for the self-assembly of oligonucleotide molecules and hence, the DNA can also non-specifically adsorb to the bare gold surface.

In one approach, a bifunctional linker is used to attach 5'-thiol-modified oligonucleotide sequences to reactive pads of amino-alkanethiol. The bifunctional linker preferably contains a functionality reactive towards amines and a functionality reactive towards amino-alkanethiols. The surface is first exposed to a solution of the linker, whereby one end of the molecule reacts with the amino-alkanethiol surface. Excess linker is rinsed away and the array surface is then spotted with 5'-thiol-modified nucleic acid which reacts with the other end of the bifunctional linker, forming a covalent bond between the nucleic acid and the surface monolayer.

Step (6). In step 6 the protecting group (Fmoc) is removed from the array surface. Preferably, this is accomplished by exposure to a 1M solution of the secondary amine, TAEA, in DMF. Many basic secondary amines can be used to remove Fmoc from the surface; for example, 1 M solutions of ethanolamine and piperidine can be used with equal success. TAEA was chosen specifically as the deprotection agent since it effectively scavenges the dibenzofulvene byproduct and is efficiently rinsed from the array surface. After this deprotection step, the array background has been converted back to the original ω-modified alkanethiol surface.

Step (7). In the final step of the array fabrication, the ω-modified alkanethiol background is reacted with a compound to create a background that is resistant to the non-specific binding of proteins. The preferred compound for this purpose is PEG-NHS, although any compound which will selectively bind to the ω-modified alkanethiol surface and inhibit non-selective protein binding can be used. In order to monitor the binding of proteins to arrays of surface-bound biomolecules or cells, it is critical that the array background prohibit the non-specific adsorption of protein molecules. Significant amounts of such non-specific binding obscures the measurement of small amounts of protein binding at specific array locations.

To create a background that is resistant to the non-specific binding of proteins, the MUAM surface was reacted with PEG-NHS. As was the case in the Fmoc-NHS+MUAM reaction, PEG-NHS reacts with the terminal amine groups of the MUAM to form an amide linkage, covalently attaching the PEG polymer chain to the surface. The preferred PEG-NHS polymer has an average molecular weight of 2000 and contains one NHS ester moiety per molecule, allowing for a single point of attachment. After the reaction of the deprotected surface with PEG-NHS, the surface remains hydrophilic and has a measured contact angle of 37.3°±2.6°. A total thickness of 23.8 Å±0.8 Å was measured for a MUAM monolayer film after reaction with PEG-NHS. This increase of only 6 Å of PEG suggests that only a small fraction of the amine groups of the MUAM are modified and that the oligo(ethylene glycol) chains are lying flat across the surface.

Alternatively, the reverse of this maleimide-modified surface chemistry can be used to create active sulfhydryl-terminated monolayers that can be used to attach biopolymers onto metal (preferably gold) surfaces. Other researchers have also created thiol-terminated monolayers on gold surfaces, but this was accomplished via direct adsorption and self-assembly of an alkane dithiol on the surface, Kohli et al. (1998). In contrast, the reaction scheme utilized in the present approach (see FIG. 1) employs a self assembled MUAM monolayer that is then reacted with the molecule N-succinimidyl-5-acetylthiopropionate (SATP). The NHS ester moiety of SATP forms an amide bond with the ω-amino groups of the monolayer and creates a protected sulfhydryl-terminated surface. The protecting group can be removed in alkline solution to create an active surface.

Biopolymers can be attached onto these surfaces by two possible strategies: (i) reacting the sulfhydryl-terminated monolayer with maleimide-modified target biomolecules; or (ii) performing a thiol-disulfide exchange reaction with thiol-modified biomolecules to create a surface disulfide linkage. The latter surface attachment scheme has the advantage of being reversible; the cleavage of the immobilized disulfide in the presence of dithiothreitol (DTT) releases the attached biomolecule and restores the sulfhydryl-terminated monolayer.

In the case of adhering GSH to the substrate, the disulfide exchange reaction is preferred because the GSH includes a thiol group that will readily react with the intermediate disulfide. The GSH can also be modified to include a linker, as noted above, with the linker incorporating a maleimide moiety. In this instance, the maleimide approach is used to immobilize the GSH onto the substrate.

As detailed in the Examples, a variety of spectroscopic techniques were employed to characterize these two surface attachment chemistries. PM-FTIRRAS was used to monitor the chemical structure of the self-assembled monolayer at each step of the attachment process. The hybridization of fluorescently labeled DNA molecules onto oligonucleotide monolayers created by the thiol-disulfide exchange reaction was determined by fluorescence "wash-off" measurements. These solution fluorescence measurements provide an estimate of the surface coverage of immobilized DNA. In a final set of Examples, the thiol-disulfide exchange reaction was used to fabricate a two-component DNA microarray on a thin gold film, and SPR imaging measurements were used to monitor the hybridization of complementary DNA sequences onto this DNA array in situ.

Array elements can be individually spotted using as little as 40 nL of target sample solution. This permits the label-free detection of as little as 2 femtomole of DNA per array spot.

A major advantage of SPR imaging as opposed to conventional SPR angle techniques is its ability to create built-in controls within the array itself to distinguish between specific and non-specific surface interactions. With this ability in hand, reaction parameters can, for example, easily be optimized to maximize the specificity of the hybridization. In the case where nucleic acids are either immobilized on the substrate or otherwise involved in the reaction being studied, the stringency of the hybridization reaction is affected by a number of parameters, the most notable being temperature, salt concentration, pH, and the presence of denaturants such as urea or formamide. Increasing the salt concentration generally results in more target DNA adsorption to both the matched and mismatched spots (i.e., both specific and non-specific adsorption is increased). Decreasing the salt concentration below 200 mM generally results in less hybridization to the perfect match. Where high discrimination is required (as when probing for closely related sequences), more stringent conditions may be necessary. One of skill in the art is capable of systematically varying one parameter at a time to arrive at an optimum set of reaction conditions (temperature, salt concentration, pH, and presence of denaturants) for any given analysis.

The arrays described herein may also be fabricated using micro-fluidic channels to define the discrete domains of GSH. In one variation of this approach, a thin film having disposed therein one or more micro-grooves is reversibly attached (in face-to-face orientation) to a chemically-modified metal substrate as described above, thereby defining one or more micro-channels. It is preferred that the thin film be made from PMDS. Then, one or more biomolecules, such DNA or GSH, are passed through the micro-channels such that the biomolecules bind to the surface of the chemically-modified substrate at points within the micro-channels. The thin film is then removed from the chemically-modified substrate, thereby yielding a chemically-modified substrate having deposited thereon an array of biomolecules.

Another approach using microfluidic channels comprises the same steps recited in the previous paragraph, and then, after removing the thin film from the chemically-modified substrate, reversibly attaching to the substrate (in face-to-face orientation) a second thin film having disposed therein one or more micro-grooves in such a fashion that the micro-grooves of the second thin film intersect the array of biomolecules, thereby defining a distinct set of micro-channels through which can be passed reagents that will make contact with the array of biomolecules deposited on the substrate.

EXAMPLES

The following Examples are included solely to provide a more complete understanding of the present invention. The Examples do not limit the scope of the invention disclosed and claimed herein in any fashion.

Standard Procedures:

Gold substrates used in contact angle measurements were purchased commercially from Evaporated Metal Films (Ithaca, N.Y.) and those used in scanning or imaging SPR measurements were prepared by vapor deposition onto microscope slide covers that had been silanized with (3-mercaptopropyl)-trimethoxysilane (Aldrich, Milwaukee, Wis.) in a manner similar to that reported by Goss et al. (1991).

All oligonucleotides were synthesized on an ABI (Foster, Calif.) DNA synthesizer at the University of Wisconsin Biotechnology Center. Oligonucleotides included a 5' thiol modifier C6, as well as a 15-T spacer prior to the DNA sequence of interest to provide additional spacing away from the gold surface. Glen Research's (Sterling, Va.) "5'-Thiol-Modifier C6" and ABI's "6-FAM" were used for 5'-thiol-modified and 5'-fluorescein-modified oligonucleotides respectively, and "Spacer Phosphoramidite 18" (Glen Research) was used for the addition of an ethylene glycol spacer region. Thiol-modified oligonucleotides were deprotected as outlined by Glen Research's product literature. (Glen Research Corp. (1990) "User Guide to DNA Modification and Labeling"). Before use, each oligonucleotide was purified by reverse-phase binary gradient elution HPLC (Shimadzu (Columbia, Md.) "SCL-10 AVP") and DNA concentrations were verified with an HP8452A UV-VIS spectrophotometer (Hewlett-Packard, Palo Alto, Calif.).

SPR Imaging Apparatus: The in situ SPR imaging instrument is a modified version of that described previously, Jordan & Corn (1997); Thiel et al. (1997); Jordan et al. (1997); and Frutos et al. (1998), in which the HeNe laser and beam expander have been replaced by a collimated white light source/bandpass filter combination. A more thorough discussion of this modification in the context of near IR (NIR) SPR imaging is reported elsewhere, see Nelson et al. (1999). In short, a collimated, polychromatic beam of light was used to illuminate an SF10 prism/Au/thin film/buffer assembly at a fixed incident angle near the SPR angle. The reflected light was passed through a 10 nm bandpass filter (830 nm) and was collected with an inexpensive CCD camera. Differences in the reflected light intensity measured at various locations on the sample create the image and are a direct result of differences in the thickness or refractive index of the material bound at the gold surface. Data work-up was done using NIH Image v. 1.61 software.

Materials:

N-succinimidyl S-acetylthiopropionate (SATP, Pierce), sulfosuccinimidyl 4-(N-maleimidomethyl) cyclohexane-1-carboxylate (SSMCC, Pierce), N-ethyl maleimide (Aldrich), triethanolamine hydrochloride (TEA, Sigma), dithiothreitol (DTT, Aldrich), 2,2-dipyridyl disulfide (DPDS, Aldrich), ethylenediaminetetraacetic acid disodium salt dihydrate (EDTA, Aldrich), potassium hydroxide (Aldrich), disodium hydrogen phosphate dihydrate (Fluka, a wholly-owned subsidiary of Sigma-Aldrich), sodium dihydrogen phosphate monohydrate (Fluka), N,N-dimethylformamide (DMF, Aldrich), 1-octadecanethiol (ODT, Aldrich), magnesium chloride (Sigma), and sodium dodecylsulfate (SDS, Fluka) were used as received.

| The 5' thiol-modified DNA sequences: | |
|---|---|
| GTG TTA GCC TCA AGT G; | SEQ. ID. NO:1: |
| GTC TAT GCG TGA ACT G; and | SEQ. ID. NO:2: |
| GTG TAT CCG ACA TGT G | SEQ. ID. NO:3: | were synthesized at the University of Wisconsin Biotechnology Center as noted above.

To verify the presence of thiol, Ellman's reagent was used.
The complementary sequences:

| CAC TTG AGG CTA ACA C (complement to SEQ. ID. NO:1); | SEQ. ID. NO:4: |
|---|---|
| CAG TTC ACG CAT AGA C (complement to SEQ. ID. NO:2); and | SEQ. ID. NO:5: |
| CAC ATG TCG GAT ACA C (complement to SEQ. ID. NO:3) | SEQ. ID. NO:6: | were also synthesized at the University of Wisconsin Biotechnology Center.

Amino-modified DNA (Integrated DNA Technologies, Coralville, Iowa) with a 5' amino modifier, C6: $(T)_{15}$GTC TAT GCG TGA ACT G (SEQ. ID. NO: 7), was used in the synthesis of maleimide-modified DNA. Before use, each oligonucleotide was purified using reversed phase binary elution HPLC (Shimadzu SCL1OAVP) and the concentration was determined using a HP8452A UV-vis spectrophotometer to monitor the absorption at 260 nm. 11-Mercaptoundecylamine (MUAM) was a generous gift from Professor Whitesides at Harvard University. Commercially available MUAM (Dojindo Laboratories, Taburu, Japan) was also used. Commercial gold slides (5 nm Cr and 100 nm Au) were purchased from Evaporated Metal Films (New York) and were used for all PM-FTIRRAS measurements.

Preparation of the Free Sulfhydryl Surface:

The MUAM monolayer was prepared by soaking a gold slide in an ethanolic solution of 1.0 mM MUAM for at least 24 hr. See FIG. 1, step A. The reaction of the amine surface with the NHS ester of SAT? was carried out by spotting 2.0 mM SATP in 10% DMF and 90% 0.1M TEA buffer solution (pH7.0) on the slide for 1–2 hr. See FIG. 1, steps A→B. For the sulfhydryl deprotection, the surface was soaked in a solution of 0.5 M hydroxylamine, 0.05 M DTT, 0.05 M phosphate buffer and 0.025 M EDTA at pH 7.5 for 20 min. See FIG. 1, steps B→C.

Sulfhydryl Surface Reactions:

A 10 mM N-ethyl maleimide and 0.1 M TEA buffer (pH 7.0) solution was reacted on the surface for 30 minutes for the N-ethyl maleimide addition to the sulfhydryl surface. See FIG. 1, steps C→D. Maleimide DNA was synthesized by reacting 50% 10 mM SSMCC and 50% amino-modified DNA, both in 0.1 M TEA buffer pH 7.0, for 3.5 hours. This was followed by HPLC purification of the DNA. For the maleimide-modified DNA addition to the sulfhydryl monolayer, a 30 µM solution of the modified DNA was reacted on the surface overnight.

2,2-dipyridyl disulfide 1 mg/ml was reacted with the thiol surface in a 1:1 mixture of 0.1 M TEA buffer solution (pH 8.0) and DMF for 2 hrs to create the intermediate disulfide linkage. See FIG. 1, steps C→E. The reaction of thiol-modified DNA on the disulfide surface was carried out by spotting 1 µl of 1 mM DNA in 0.1 M TEA (pH 8.0) buffer, and then covering the surface with a glass slide in a humidity chamber for at least 6 hrs. See FIG. 1, steps E→F. The surface was then immersed for 1 hr in a buffer solution containing 20 mM sodium phosphate, 100 mM NaCl and 1 mM EDTA (pH 7.4) to remove any non-specifically adsorbed DNA molecules from the surface. Reduction of the disulfide bonds between DNA and the sulfhydryl surface was accomplished by exposing the surface to 50 mM DTT in 0.1 M TEA (pH 7.0). Between each reaction step the samples were thoroughly rinsed with water and dried under a stream of nitrogen.

PM-FTIRRAS Surface Characterization:

Between each reaction step, PM-FTIRRAS measurements were collected using a Mattson RS-1 spectrometer with real-time interferogram sampling electronics and optical layout as described previously. See Barner et al. (1991) and Green et al. (1991). Spectra were collected from 1000 scans with a resolution of 4 $cm^{-1}$ using a narrow-band HgCdTe detector.

Fluorescence "Wash-Off" Measurements:

The surface density of oligonucleotide monolayers created by the thiol-disulfide exchange reaction was estimated by measuring the fluorescence of a solution used to "wash off" the fluorescently labeled complement to the surface immobilized strand. To do this, a single-stranded DNA surface comprising SEQ. ID. NO: 3 was coated with 2 µM fluorescently-labeled complement (SEQ. ID. NO: 6), and covered with a glass slide to evenly distribute the solution across the surface. After hybridizing for 20 min, the surface was soaked in a solution of 0.2% SDS/2×SSPE (from 20×SSPE buffer: 3.6 M NaCl, 0.2 M $NaH_2PO_4$, 0.02 M EDTA, pH 7.7) for 10 min to remove non-specifically adsorbed fluorescent complement. Next, the slide was immersed for 20 min in 7 ml of a solution containing 50 mM KOH to denature the DNA. The fluorescence emission at 517 nm was measured with a Hitachi F-4500 fluorescence spectrophotometer for each denaturing solution.

Array Fabrication and Characterization:

Gold films (45 nm) with a thin chromium underlayer (5 nm) on SF10 glass slides (Schott Glass Technologies, Duryea, Pa.) were used for SPR imaging measurements. A self-assembled monolayer of 1-octadecanethiol (ODT) was formed by soaking the sample overnight in a 1 mM ethanolic solution of the alkanethiol. Portions of the ODT monolayer were removed by irradiating the sample through a quartz mask with UV light from a mercury-xenon arc lamp for 1.5 hrs. The surface was then immersed in a 1 mM ethanolic solution of MUAM for 2 hrs. See Brockman et al. (1999). This resulted in a hydrophobic background of ODT and 500 µm×500 µm MUAM squares. The reaction steps described above, leading to the formation of the surface disulfide using 2,2-dipyridyl disulfide (DPDS), were then carried out on the MUAM array elements by applying the reaction solutions using a pneumatic pico pump to deliver 40 nL solution volumes to the surface (World Precision Instruments). Solutions of thiol-modified DNA (SEQ. ID. NOS: 1 and 2) were spotted onto the disulfide surface, and the thiol-disulfide exchange reaction was allowed to proceed overnight. The surface was then used immediately for SPR imaging experiments.

The in situ SPR imaging apparatus has been reported elsewhere, see Brockman et al. (1999). Briefly, polarized collimated white light incident on a prism/Au/thin film/buffer assembly was set at a fixed angle. Light reflected from this assembly was sent through a band-pass filter and collected by a CCD camera. Complementary DNA at a concentration of 1 µM was introduced to the sample surface and left to react for 10 mm. The surface was rinsed with phosphate buffer prior to collecting an SPR image. The double-stranded DNA was then denatured with 8 M urea for 15 minutes to regenerate the single-stranded DNA array. At this point the hybridization cycle was repeated.

Sulfhydryl Monolayer Formation:

The reaction scheme for the surface modification of MUAM to a sulfhydryl-terminated monolayer is shown in FIG. 1 (Steps A–C). SATP is a heterobifunctional cross-linking agent containing a protected sulfhydryl group and an active NHS ester. The NHS ester functionality reacts with the primary amine surface of MUAM in a slightly alkaline solution (pH 7–9), forming amide bonds and a protected sulfhydryl functionality on the terminal end of the monolayer. The acetyl protecting group is removed by exposing the surface to a hydroxylamine solution, which has added DTT to prevent the formation of surface disulfide bonds.

The SATP attachment onto a MUAM self-assembled monolayer and the SATP deacetylation reaction were characterized by PM-FTIRRAS. The PM-FTIRRAS spectrum of a MUAM monolayer (FIG. 2A) shows several weak bands in the region from 2000 to 1000 cm$^{-1}$. Bands at 1615 and 1517 cm$^{-1}$ are assigned to the NH$_3^+$ asymmetric and symmetric deformations, respectively; while the methylene scissor deformation and twisting modes are seen at 1467 and 1264 cm$^{-1}$ (see Table 1 for band assignments).

TABLE 1

PM-FTIRRAS Band Assignment of Surface Modification with Maleimide Reaction Probes.

| Surface | Wavenumber (cm$^{-1}$) | Assignment | Figure |
|---|---|---|---|
| MUAM | 1615 | NH$_3^+$ asymmetric deformation | 2A |
|  | 1517 | NH$_3^+$ symmetric deformation |  |
|  | 1467 | CH$_2$ scissors deformation |  |
|  | 1264 | CH$_2$ twist |  |
| SATP | 1750 | C=O symmetric stretch | 2B |
|  | 1696 | C=O asymmetric stretch |  |
|  | 1660 | amide I |  |
|  | 1550 | amide II |  |
|  | 1444 | CH$_2$ scissors deformation |  |
|  | 1360 | CH$_2$ wagging |  |
|  | 1140 | C—O stretch of tertiary amine |  |
| N-ethyl maleimide | 1787 | C=O symmetric stretch | 3(D–C) |
|  | 1710 | C=O asymmetric stretch |  |
|  | 1405 | CH$_2$ scissors deformation |  |
|  | 1360 | CH$_2$ wagging |  |
|  | 1228 | C—N stretch |  |
| Maleimide-modified DNA | 1780 | C=O symmetric stretch | 4(D–C) |
|  | 1709 | C=O asymmetric stretech and double bond stretching vibrations of the DNA bases |  |
|  | 1273 | NH bending of thymine |  |
|  | 1221 | Asymmetric stretch of phosphate |  |
|  | 1074 | Symmetric stretch of phosphate |  |

This spectrum is similar to that previously reported. See Brockman et al. (1999). The covalent attachment of SATP to the MUAM monolayer gives characteristic amide bands (amide I and II) (FIG. 2, trace B) that results from the formation of an amide linkage between the NHS ester of the SATP molecule and free amine groups on the surface. Also, a prominent carbonyl stretching feature arises from the acetyl protecting group on SATP at 1696 cm$^{-1}$. Two additional bands at 1360 and 1140 cm$^{-1}$ are assigned to the CH$_2$ wagging and C—O stretching modes of the acetyl group, respectively. After deprotection, the carbonyl band (1696 cm$^{-1}$) FIG. 2, trace C) disappears, as expected, due to the removal of the acetyl protecting groups from the surface. A difference spectrum between the deprotected and protected SATP monolayer shows the elimination of the bands at 1796, 1554, 1360 and 1140 cm$^{-1}$, suggesting that a successful deprotection reaction has occurred (FIG. 3, bottom trace). There was no change in the amide I and II bands during the deprotection process, indicating that SATP did not desorb from the MUAM surface. These measurements suggest that SATP has robustly added to the primary amine groups on the surface, and that the sulfhydryl group can be deprotected without affecting the amide bond. These same reactions could also be used with amine-terminated bilayers created from mercaptoundecanoic acid (MUA) and poly-L-lysine as a second method for creating sulfhydryl terminated gold surfaces. See Frey et al. (1995).

Maleimide Attachment Chemistry:

Once the sulfhydryl monolayer has been formed, the terminal thiol is free to undergo alkylation with molecules that contain maleimide groups as shown in FIG. 1, step D. The double bond of the maleimide group undergoes an alkylation reaction by forming a stable thioether bond with sulfhydryls at a neutral pH with reaction rates 1000 times greater than a maleimide reacting with amino or hydroxyl groups. Partis et al. (1983). Two maleimide-containing molecules were immobilized to the surface using this attachment strategy: N-ethyl maleimide and maleimide-modified DNA. The N-ethyl maleimide addition to the surface was complete in 30 minutes at a concentration of 10 mM, while the maleimide-modified DNA was reacted with the surface overnight.

Figure 2:
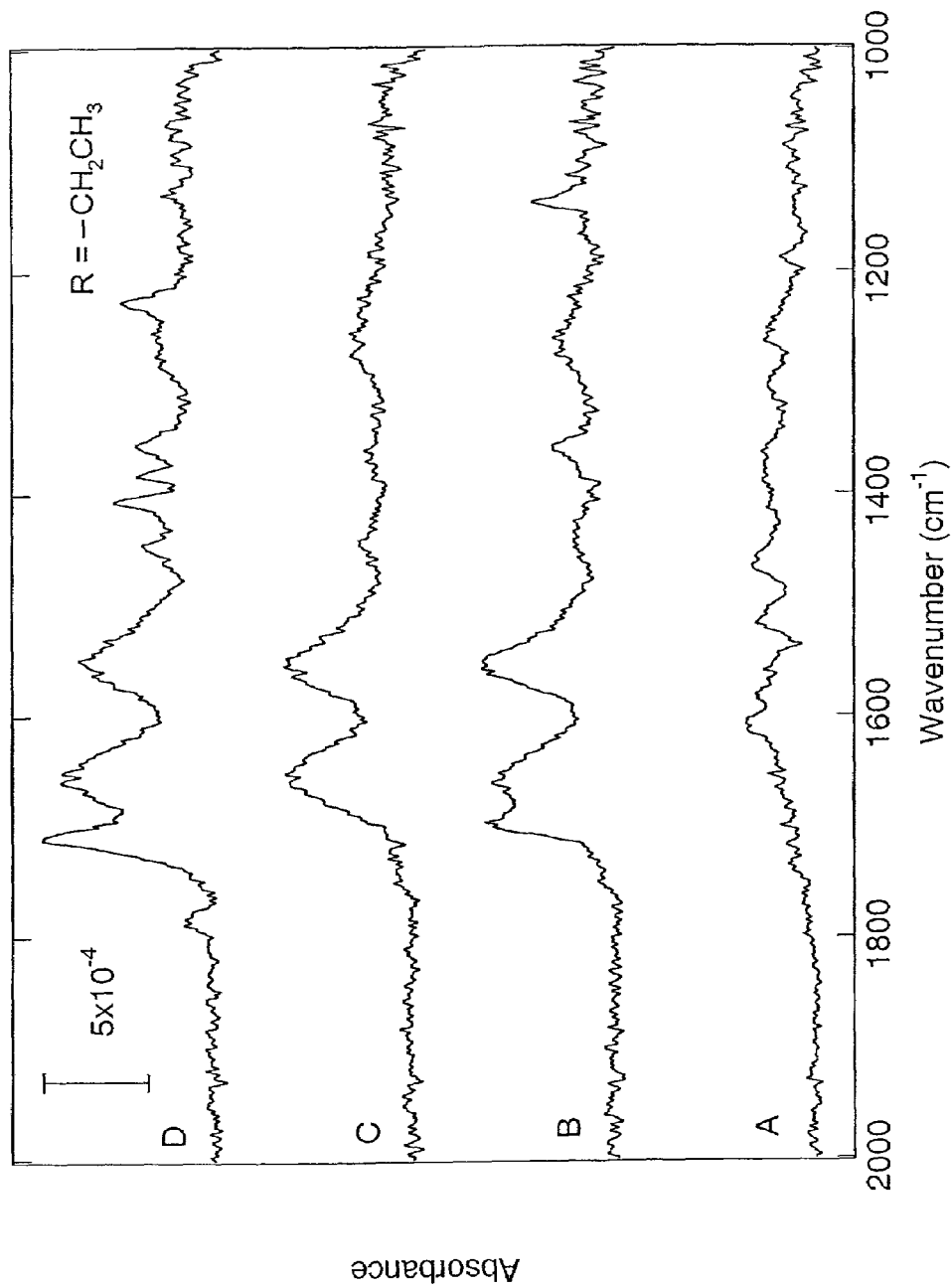
FIG. 2 is a series of PM-FTIRRAS spectra showing the MUAM surface modification process: (A) MUAM; (B) SATP attachment to MUAM surface through amide bond formation between the amine-terminated alkanethiol and the NHS ester in SATP; (C) the active sulfhydryl surface is obtained after deprotection of SATP; and (D) reaction of thiol groups with N-ethyl maleimide molecules to form stable thioether linkages. See Table 1 for band assignments.
Figure 3:
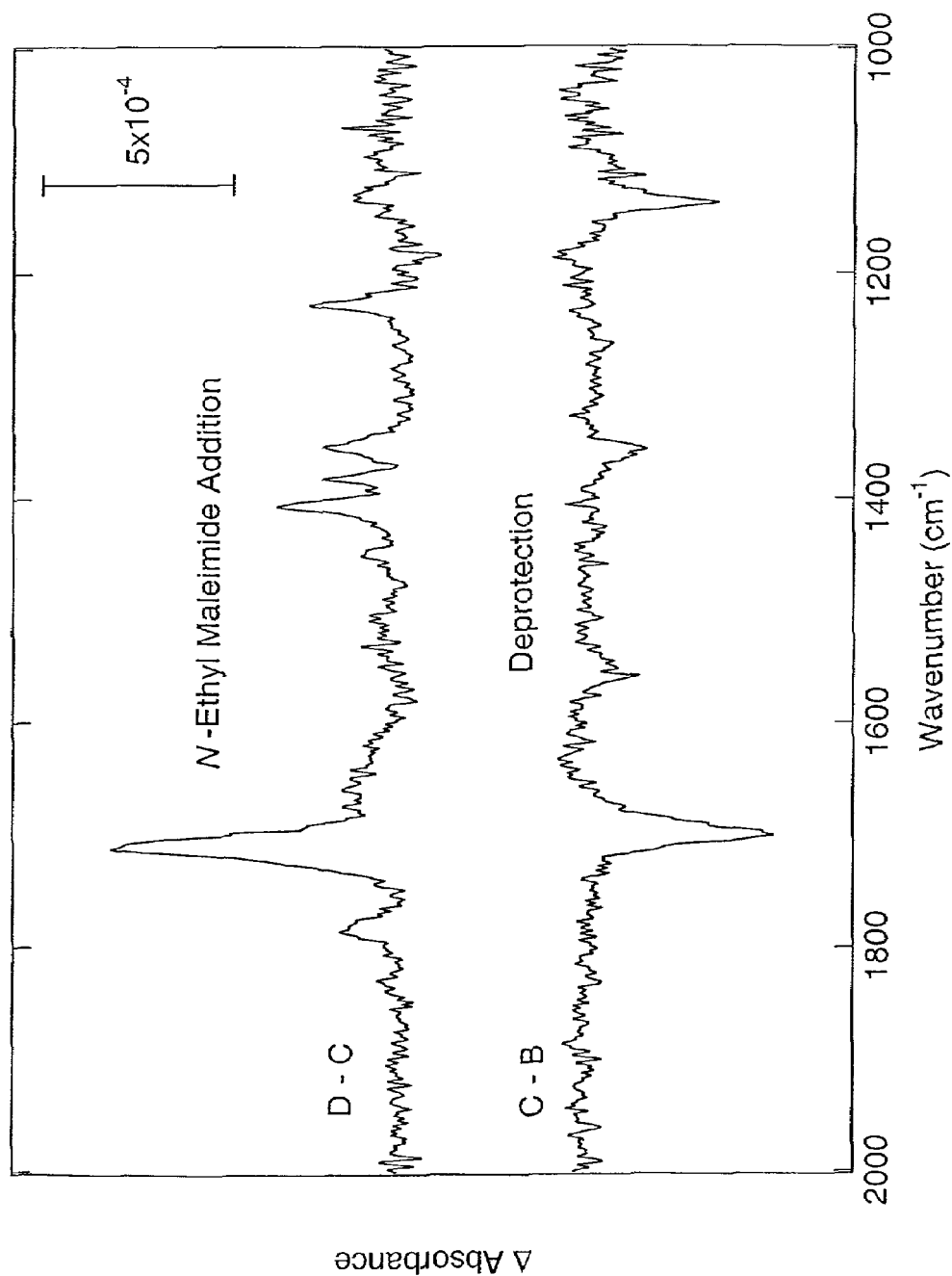
FIG. 3 is difference PM-FTIRRAS spectra of: (bottom trace) deprotected SATP surface after removal of the acetyl protecting group; (top trace) N-ethyl maleimide addition to deprotected sulfhydryl surface. The letter designations refer to the respective steps shown in FIG. 1.

FIG. 2, trace D shows the PM-FTIRRAS spectrum for the attachment of N-ethyl maleimide to the sulfhydryl surface, and FIG. 3 (top trace) shows the difference PM-FTIRRAS spectrum for this reaction. The attachment of maleimide groups onto the free sulfhydryl surface is shown by the appearance of the asymmetrical carbonyl stretching band at 1710 cm$^{-1}$. This band is due to the coupled in-phase stretching of the two maleimide carbonyls. It has a strong intensity and is very sharp for the reaction with N-ethyl maleimide. This feature was also seen with the other maleimide probe molecules that were studied. In addition, there is a less intense maleimide carbonyl symmetrical stretching mode located at 1780 cm$^{-1}$. The difference spectrum also shows extra bands featuring methylene scissoring and twisting deformations (1405 cm$^{-1}$) and wagging mode (1360 cm$^{-1}$). The band at 1228 cm$^{-1}$ is assigned to the asymmetric CNC stretching mode.

Figure 4:
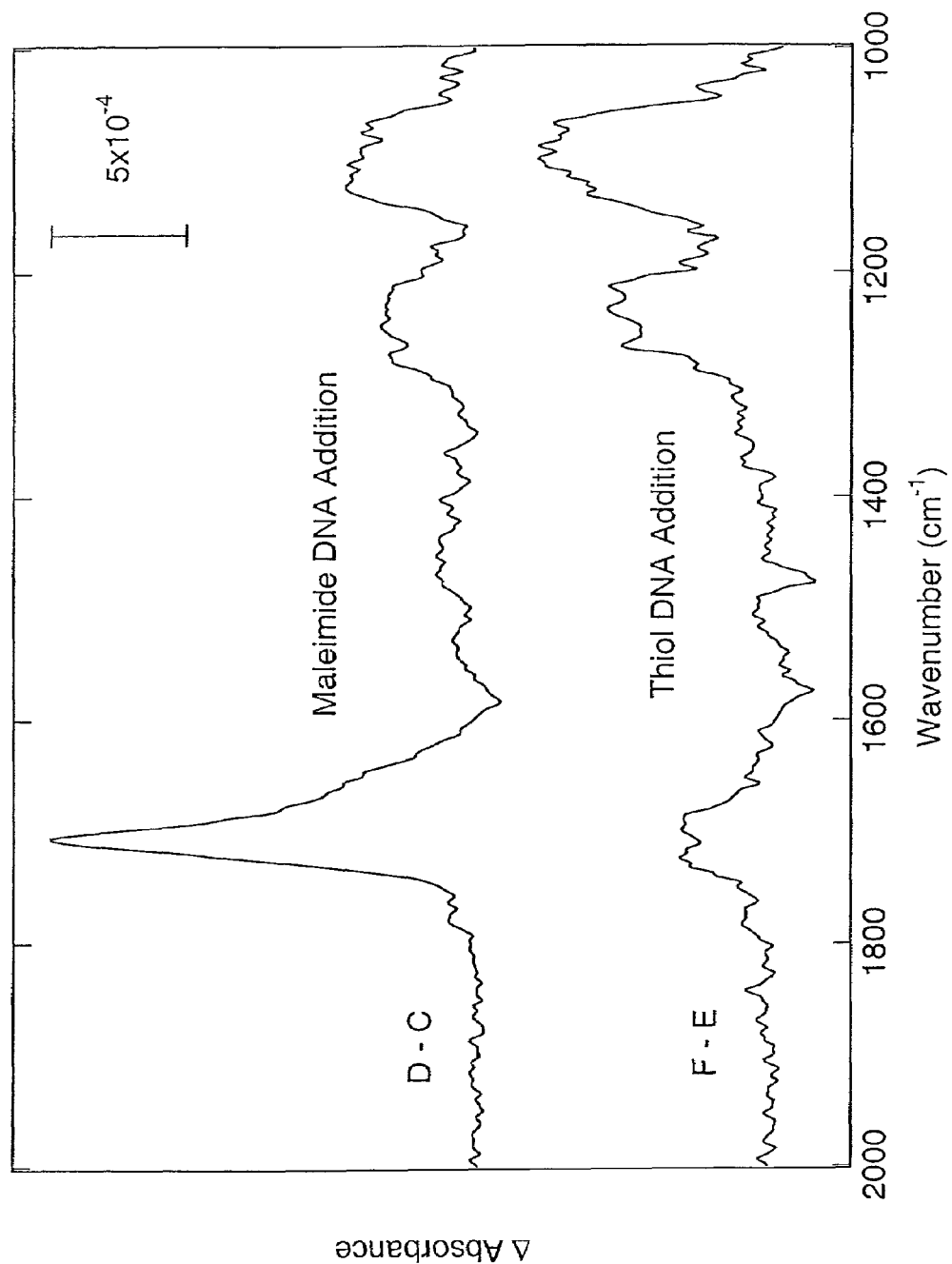
FIG. 4 is a series of difference PM-FTIRRAS spectra of DNA immobilized to the SPR-capable surface: (bottom trace): thiol-disulfide exchange reaction with the pyridyl disulfide surface and thiol-modified DNA; (top trace): maleimide-modified DNA addition to the deprotected sulfhydryl surface. The letter designations refer to the respective steps shown in FIG. 1.

The difference spectrum for the maleimide-modified DNA attachment to the sulfhydryl surface is shown in FIG. 4 (top). The sharp peak at 1709 cm$^{-1}$ is assigned to the carbonyl asymmetric stretching feature of the maleimide group; the double bond stretching vibrations of the DNA bases also contributes to this peak. The 1709 cm$^{-1}$ peak, along with a weaker symmetric carbonyl stretching feature at 1780 cm$^{-1}$, indicates that maleimide has been immobilized on the surface. The peaks at 1221 and 1074 cm$^{-1}$ are assigned to the asymmetric and symmetric stretching vibrations of the phosphate in the DNA backbone, respectively. The peak at 1273 cm$^{-1}$ is assigned to the NH bending vibration on the base thymine.

This Example clearly demonstrates that the maleimide attachment route can be used to immobilize maleimide-modified nucleic acids to an SPR-capable substrate.

Disulfide Attachment Chemistry:

In addition to the maleimide surface attachment strategy, thiol-containing biomolecules can be immobilized by a disulfide linkage onto the surface. This surface disulfide attachment of a biomolecule is created in a two-step process shown in FIG. 1, steps E and F. The first step (step E) is a thiol-disulfide exchange reaction of the sulfhydryl surface with the disulfide DPDS to create a pyridyl disulfide surface. The leaving group for this surface reaction, pyridine-2-thione, is not capable of reacting with the resulting disulfide on the surface. In the second reaction step (step F), the pyridyl disulfide on the surface is exchanged with a thiol-containing biomolecule in solution. Once again, the pyridine-2-thione leaving group of this second reaction does not react with the surface.

The difference spectrum for the thiol-disulfide exchange reaction of thiol-modified DNA (thiol-modified SEQ. ID. NO: 3) and a pyridyl disulfide surface is shown in FIG. 4 (bottom trace). The appearance of four IR absorption bands in the spectrum indicates that DNA has been immobilized on the surface. The absorptions at 1704 and 1278 cm$^{-1}$ are assigned to the double bond stretching vibration of the DNA bases and NH bending vibration on the base thymine, respectively. The bands at 1220 and 1070 cm$^{-1}$ are assigned to the asymmetric and symmetric stretching vibrations of phosphate, respectively.

The surface coverage of DNA immobilized using the thiol-disulfide exchange reaction was estimated by quantifying "washed-off" fluorescently-labeled complement (SEQ. ID. NO: 6) with solution fluorescence measurements. The fluorescently-labeled complement was hybridized to the surface, then removed in a denaturing solution and measured versus standards. Using this method, the surface coverage of the immobilized DNA was estimated to be $1.5 \times 10^{12}$ molecules/cm$^2$, assuming a 100% hybridization efficiency. Hybridization efficiency of surface immobilized DNA has typically been found to be about 60% ±20%, Jordan et al. (1997). Therefore, the above number can be considered the lower limit for the surface coverage of DNA immobilized in this manner. Typical DNA surface coverages using other attachment strategies have been measured in the range of from about $3.0 \times 10^{12}$ to about $1.5 \times 10^{13}$ molecules/cm$^2$ (Jordan et al., 1997).

The thiol-modified DNA attached to the surface with a disulfide linkage can be removed when the surface is exposed to DTT. See FIG. 1, steps F→C. The PM-FTTR-RAS difference spectra taken before and after exposing the disulfide attached DNA surface to DIT showed the elimination of the characteristic DNA bands (spectra not shown). This indicates that the DNA was cleaved from the surface and that the sulfhydryl surface was regenerated. These results show that the disulfide-modified surfaces prepared as in this Example can be used to immobilize thiol-containing biomolecules on an SPR-capable surface, in a reversible fashion.

DNA Array Fabrication and SPR Imaging Measurements:

An important application of the DNA surface attachment chemistry described in the previous Examples is the fabrication of DNA microarrays on thin metal (preferably gold) films for SPR imaging measurements of biopolymer adsorption. This Example demonstrates that the disulfide DNA attachment chemistry can be used in a multi-step fabrication process to create DNA microarrays, and that these arrays can be used in a reversible fashion to monitor the hybridization adsorption of complementary DNA molecules onto a gold surface with SPR imaging.

A DNA microarray was fabricated on a 45 nm thin gold film using a combination of self-assembly, photopatterning, and the disulfide attachment chemistry described in the previous Example. This fabrication process was similar to one previously described in U.S. Pat. No. 6,127,129. On a thin gold film, a hydrophobic background was created by the self assembly of a monolayer of octadecanethiol (ODT). This monolayer was photopatterned to create 500 μm×500 μm squares that were filled in with MUAM. Each MUAM array element could then be reacted separately by spotting 40 nL of solution to each array spot. The ODT background prevented the spread of the reaction solutions outside the array elements; other hydrophobic monolayers have also been used with the same effect.

The DNA array was created by reacting each MUAM square with SATP, deprotecting the SATP to generate the sulfhydryl surface, followed by the formation of the surface disulfide using DPDS, and finally, the thiol-disulfide exchange with thiol-modified oligonucleotides. Two nucleotides (SEQ. ID. NOS: 1 and 2) of 16 base thiol-modified DNA were reacted on the disulfide surface following the pattern depicted in FIG. 5.

Figure 5A:
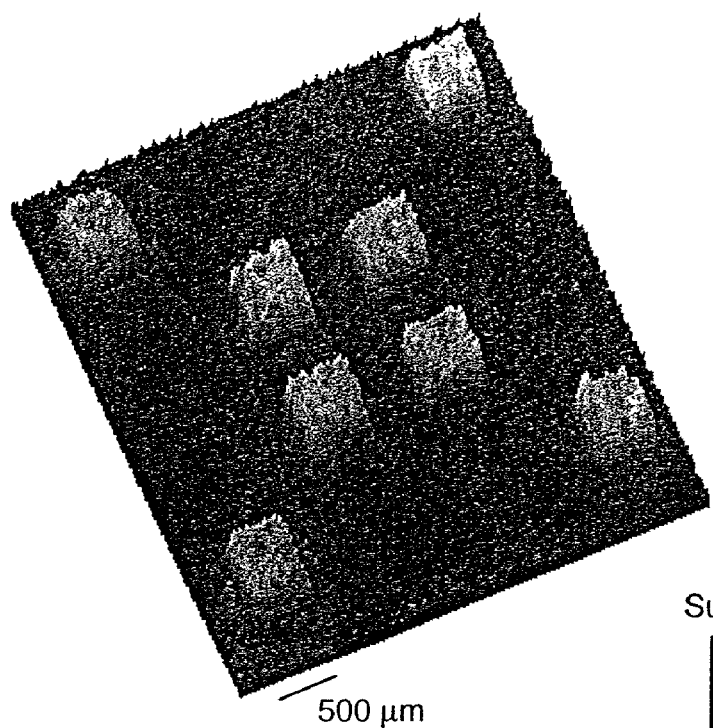
FIGS. 5A and 5B are SPR difference images of a DNA array containing two sequences of thiol-modified DNA (SEQ. ID. NOS: 1 and 2) reacted with the pyridyl disulfide surface.
Figure 5B:
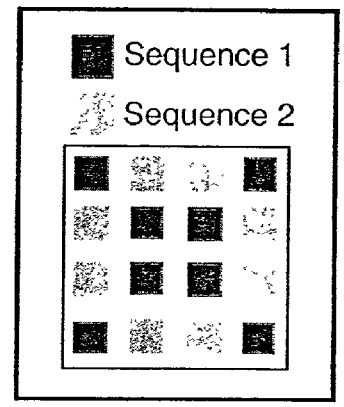
Figure 5B:
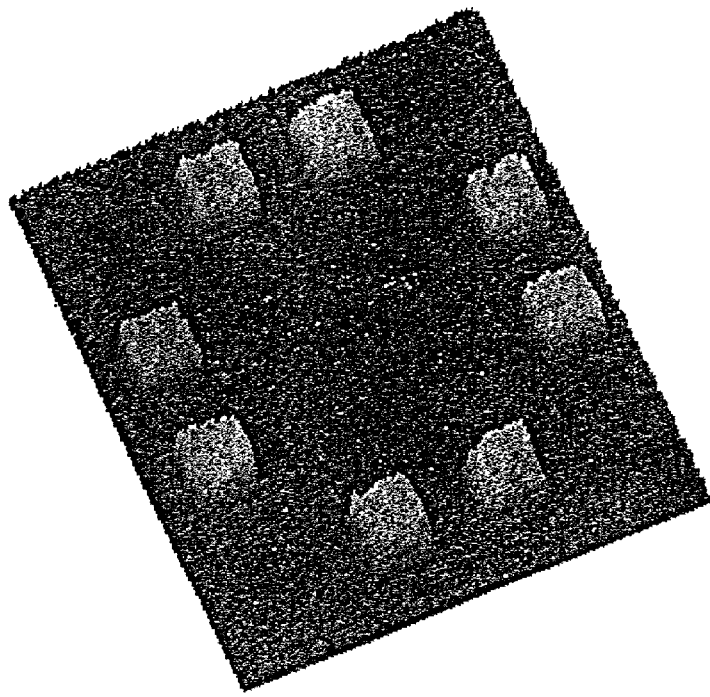

The results of SPR imaging measurements obtained from this DNA microarray are shown in FIGS. 5A and 5B. The pictures are SPR reflectance difference images obtained by subtracting the SPR image taken before and after exposing the array to one of the complementary DNA sequences (FIG. 5A is the array after exposure to SEQ. ID. NO: 4, the complement of SEQ. ID. NO: 1), and after denaturing the first complement and introducing the second complement (FIG. 5B is the array after denaturation and subsequent exposure to SEQ. ID. NO: 5, the complement of SEQ. ID. NO: 2).

The images in FIGS. 5A and 5B clearly show that an array fabricated in this manner has good hybridization specificity, i.e. there is little or no binding of the complement to the mismatched sequence, and that the hybridization is reversible. It is possible to perform several hybridization cycles using the same array without degradation of the signal. With the addition of DTT to the surface, there was a decrease in the SPR signal for all array spots, confirming the release of DNA from the surface and the cleavage of the disulfide bond (data not shown).

The above Examples show that a relatively simple approach to the attachment of biomolecules onto gold surfaces utilizing sulfhydryl-terminated monolayers is possible. The above Examples further demonstrate that the sulfhydryl surfaces react with compounds containing a maleimide functionality, thereby to form a thioether bond. In a second surface attachment strategy, the sulfhydryl surfaces were used to attach thiol-containing compounds via a disulfide linkage. This attachment strategy is useful for the preparation of DNA arrays, as well as arrays of other biomolecules such as glutathione, cysteine-containing polypeptides, and any other thiol-containing compound. Additionally, the ability to cleave the surface disulfide bond and the subsequent release of the biomolecule is useful for both the characterization of these films and their implementation in various biosensor applications.

Figure 8:
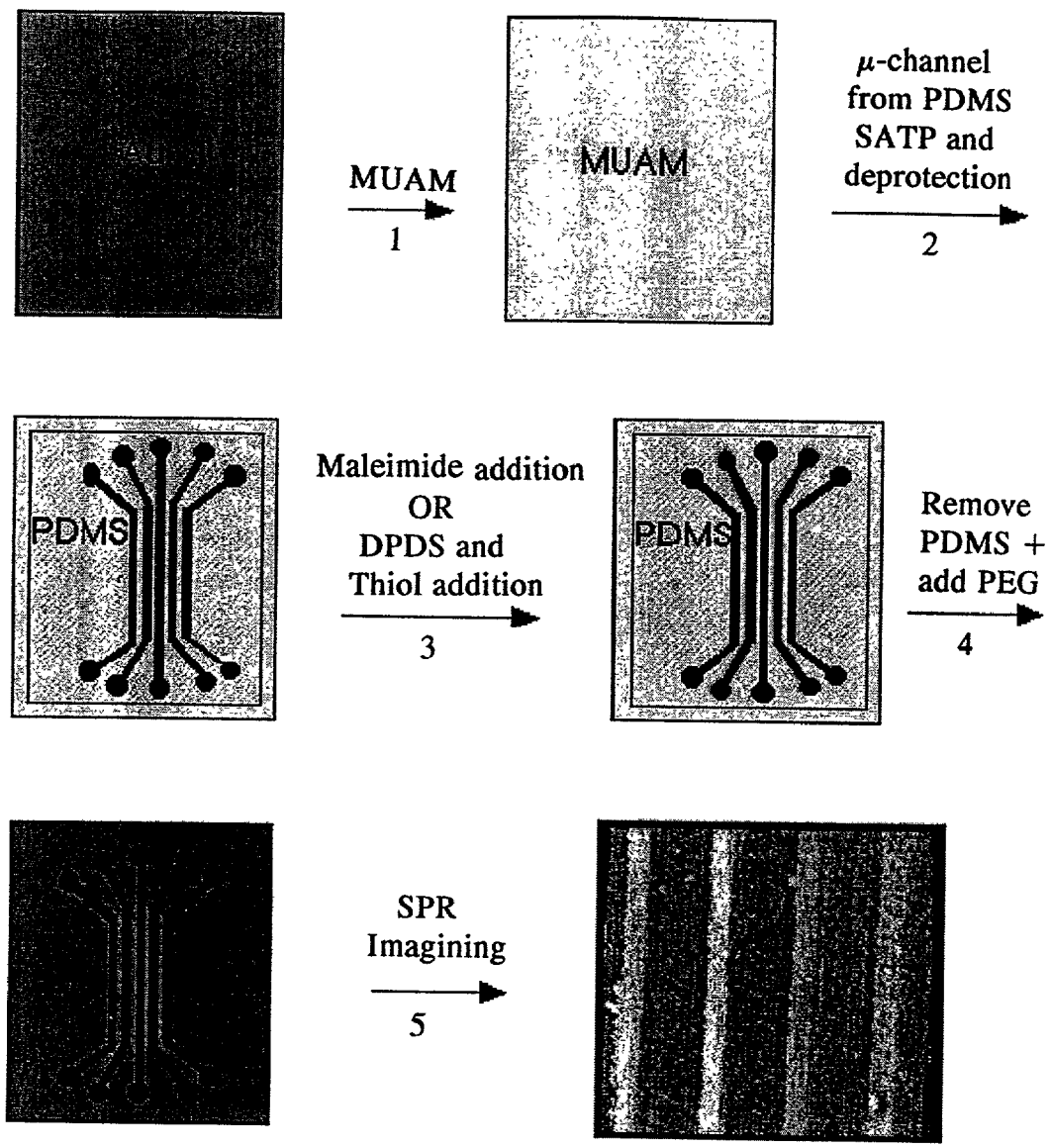
FIG. 8 is a schematic representation of a fabrication methodology used for creating 1-dimensional and 2-dimensional nucleic acid micro-arrays on a chemically-modified metal surface.

Demonstration of 1-Dimensional Array for Detection Nucleic Acids:

Referring now to FIG. 8, this figure shows a fabrication methodology according to the present invention that uses micro-fluidic channels in PDMS to define the boundaries of the discrete domains of immobilized compounds that are to form the array. This fabrication route proceeds as follows:

(1) A gold thin film surface was reacted with an amine-terminated alkanethiol (MUAM) from a 1 mM ethanolic solution for two hours in order to form a self-assembled monolayer on the gold surface.

(2) PDMS micro-channels were fabricated using a previously-described 1:1 photolithography technique, Anderson et al. (2000), and then attached to the MUAM-modified gold surface. A surface pattern was created by flowing a hetero-bifunctional linker, N-succinimidyl-5-acetylthiopropionate (SATP), through the PDMS micro-channels over the gold surface. The SATP reacts with the MUAM to create a surface coated with protected thiol groups. The protected thiol groups are then deprotected. (See also step C of FIG. 1).

(3) At this point, treatment of the substrate can diverge and follow either step D of FIG. 1, or steps E–F of FIG. 1. Thus, for example, a solution of maleimide can be flowed through the PDMS micro-channels. Or a desired biomolecule can be reacted directly with the unprotected thiol layer. Alternatively, a disulfide (such as DPDS) can be flowed through the channels, followed by passing a thiol-containing compound through the channels. Either route will result in immobilizing the molecules passed through the PDMS micro-channels to the surface. The SPR substrate illustrated in FIG. 8 was generated using SATP to form an unprotected thiol surface in step 2, followed by treatment with DPDS, and then GSH in step 3, thereby generating an SPR-capable substrate having GSH moieties immobilized thereon.

(4) After cleaning the micro-channels with water, the PDMS was removed from the surface and the gold slide soaked in a PEG-NHS solution to modify the MUAM background. This PEG-coated background is used to resist any non-specific adsorption during the subsequent experiments. The substrate was then contacted with a solution containing 500 mM of the VanR-GST fusion protein described hereinabove. The substrate was then rinsed with water and subjected to SPR imaging analysis. An SPR image of the resulting surface is shown in the final panel of FIG. 8.

Bibliography

Amann et al. (1990) *J. Bactetiol.* 172:762–770.
Anderson et al. (2000) *Anal. Chem.* 72:3158–3164.
Arthur et al. (1992) *J. Bacteriol.* 174:2582–2591.
Barner et al. (1991) *Anal. Chem.* 63:55–60.
Brockman et al. (1999) *J. Am. Chem. Soc.* 121:8044–8051.
Brockman et al. (2000) *Ann. Rev. Phys. Chem.* 51:41:63.
Duffy et al. (1998) *Anal. Chem.* 70:4974–4984.
Effenhauser et al. (1997) *Anal. Chem.* 69:3451–3457.
Fodor (1997) *Science* 277:393–395.
Frey et al. (1995) *Anal. Chem.* 67:4452–4457.
Frutos et al. (1997) *Nucleic Acids Res.* 25:4748–4757.
Frutos et al (1998) *J. Am. Chem. Soc.* 120:10277–10282.
Frutos et al. (1998) *Anal. Chem.* 70:449A–455A.
Frutos et al. (2000) *Langmuir* 16:2192–2197.
Gokce et al. (2000) *J. Mol. Biol.* 304:621–632.
Goss et al. (1991) *Anal. Chem.* 63:85–88.
Green et al. (1991) *Rev. Sci. Instrum.* 62:1426–1430.
Harboth et al. (2000) *J. Biol. Chem.* 275:31979–31985.
Herzog et al. (2000) *FEBSLett.* 472:73–77.
Hickel et al. (1989) *Nature* 339:186.
Jo et al. (2000) *Microelectrochemical Systems* 9:76–81.
Jordan et al. (1997) *Anal. Chem.* 69:4939–4947.
Jordan & Corn (1997) *Anal. Chem.* 69(7):1449–1456.
Kohli et al. (1998) *J. Am. Chem. Soc.* 120:11962–11968.
Liedberg et al. (1983) *Sensors and Actuators* 4:299.
Lin et al. (2000) *Biochem.* 39:5104–5110.
Lockhart, et al. (1996) *Nature Biotechnology* 14:1675–1680.
Martzen et al. (1999) *Science* 286:1153–1155.
Nelson et al. (1999) *Anal. Chem.* 71:3928–3934.
Nelson et al. (2001) *Anal. Chem.* 73:1–7.
Partis et al. (1983) *J. Protein Chem.* 2:263–277.
Pease et al. (1994) *Proc. Natl. Acd. Sci. USA* 91:5022–5026.
Quetglas et al. (2000) *PNAS* 97:9695–9700.
Rothenhausler & Knoll (1988) *Nature* 332:615–617.
Silin & Plant (1997) *Trends in Biotechnol.* 15.
Simons & Vander Jagt (1977) *Anal. Biochem.* 82:334–341.
Strother et al. (2000a) *Nucleic Acids Research* 28:3535–3541.
Strother et al. (2000b) *J. Am. Chem. Soc.* 122:1205–1209.
Tarlov et al. (1993) *J. Am. Chem. Soc.* 115:5305–5306.
Thiel et al. (1997) *Anal. Chem.* 69:4948–4956.
Toribio et al. (1996) *J. Chrom. B* 684:77–97.
Thomas et al. (1995) *J. Am. Chem. Soc.* 117:3830–3834.
Winzeler et al. (1998) *Science* 281:1194–1197.
Youtani et al. (2000) *IUBMB Life* 49:27–31.

What is claimed is:

1. A method of immobilizing biomolecules or cells to a metal substrate comprising:
   (a) depositing an amino-$C_8$–$C_{24}$-alkanethiol monolayer on a metal substrate;
   (b) contacting the ω-modified monolayer of step (a) with a heterobifunctional compound comprising a first moiety reactive with the ω-modified alkanethiol monolayer and a second moiety comprising a protected thiol moiety, under conditions wherein the heterobifunctional compound binds to the ω-modified alkanethiol monolayer via the first moiety;
   (c) deprotecting the second moiety of the heterobifunctional compound to yield an unprotected thiol moiety; and then
   (d) attaching a biomolecule or cell to the unprotected thiol moiety of step (c).

2. The method of claim 1, wherein in step (a), 11-mercaptoundecylamine (MUAM) is deposited on the metal substrate.

3. The method of claim 1, wherein in step (b), the ω-modified monolayer is contacted with a heterobifunctional compound wherein the first moiety comprises a succinimidyl group.

4. The method of claim 1, wherein in step (b), the ω-modified monolayer is contacted with N-succinimidyl-S-acetylthiopropionate.

5. The method of claim 1, wherein in step (d), a deoxyribonucleic acid (DNA) molecule is attached to the unprotected thiol moiety.

6. The method of claim 1, wherein in step (d), a ribonucleic acid (RNA) molecule is attached to the unprotected thiol moiety.

7. The method of claim 1, wherein in step (d), a polypeptide molecule is attached to the unprotected thiol moiety.

8. The method of claim 1, wherein in step (d), a protein molecule is attached to the unprotected thiol moiety.

9. The method of claim 1, wherein in step (d), a glutathione-containing molecule is attached to the unprotected thiol moiety.

10. A method of immobilizing biomolecules or cells to a metal substrate comprising:
    (a) depositing an ω-modified alkanethiol monolayer on a metal substrate;
    (b) contacting the ω-modified monolayer of step (a) with a heterobifunctional compound comprising a first moiety reactive with the ω-modified alkanethiol monolayer and a second moiety comprising a protected thiol moiety, under conditions wherein the heterobifunctional compound binds to the ω-modified alkanethiol monolayer via the first moiety;
    (c) deprotecting the second moiety of the heterobifunctional compound to yield an unprotected thiol moiety;
    (d) attaching a glutathione-containing molecule to the unprotected thiol moiety of step (c); and then
    (e) contacting a glutathione-S-transferase-containing (GST-containing) molecule to the glutathione-containing molecule, whereby the GST-containing molecule is reversibly adhered to the glutathione-containing molecule.

11. The method of claim 10, wherein in step (e), a glutathione-S-transferase (GST) fusion protein is contacted to the glutathione-containing molecule.

12. A method of immobilizing biomolecules or cells to a metal substrate comprising:
    (a) depositing an ω-modified alkanethiol monolayer on a metal substrate;
    (b) contacting the ω-modified monolayer of step (a) with a heterobifunctional compound comprising a first moiety reactive with the ω-modified alkanethiol monolayer and a second moiety comprising a protected thiol moiety, under conditions wherein the heterobifunctional compound hinds to the ω-modified alkanethiol monolayer via the first moiety;
    (c) deprotecting the second moiety of the heterobifunctional compound to yield an unprotected thiol moiety;
    (d) attaching a biomolecule or cell to the unprotected thiol moiety of step (c), wherein the biomolecule or cell is attached to the unprotected thiol moiety via a linker molecule.

13. The method of claim 12, wherein in step (d), the biomolecule or cell is attached to the unprotected thiol moiety via a maleimide-containing linker molecule.

* * * * *